US005851783A

United States Patent [19]

Appel et al.

[11] Patent Number: 5,851,783

[45] Date of Patent: Dec. 22, 1998

[54] METHOD FOR DIAGNOSING AMYOTROPHIC LATERAL SCLEROSIS

[75] Inventors: Stanley H. Appel; R. Glenn Smith; Enrico Stefani, all of Houston, Tex.

[73] Assignee: Baylor College of Medicine, Houston, Tex.

[21] Appl. No.: 388,179

[22] Filed: Feb. 13, 1995

Related U.S. Application Data

[63] Continuation of Ser. No. 897,893, Jun. 12, 1992, abandoned.

[51] Int. Cl.[6] ...................... G01N 33/543; G01N 33/545; G01N 33/564; G01N 33/567

[52] U.S. Cl. ...................... 435/7.92; 435/7.21; 435/7.23; 435/7.95; 435/975; 436/503; 436/504; 436/506; 436/518; 436/531; 436/811

[58] Field of Search ................................ 435/7.21, 7.23, 435/7.92, 7.95, 975; 436/503, 504, 506, 518, 531, 811; 530/300, 395, 839, 841

[56] References Cited

PUBLICATIONS

Sawada et al, Jan. 1992. Immunoglobulins from amyotrophic lateral sclerosis (ALS) patients interact with a related muscle DHP–sensitive L–type $Ca^{2+}$ channels, FASEB J 6(1):A401, Abstract #2313.

Smith et al, Dec. 1992. Serum antibodies to L–type calcium channels in patients with amyotrophic lateral sclerosis, N. Engl. J. Med. 327:1721–8.

Lennon et al. 1989 Autoantibodies bind solubilized calcium channel omega–conotoxin complexes from small cell lung carcinoma: a diagnotic aid for Lambert–Eaton myasthemic syndrome. Mayo Clin Proc 64:1498–504.

Delbono et al. Jun. 1991. IgG from amyotrophic lateral sclerosis affects tubular calcium channels of skeletal muscle. Am J Physiol 260: C1347–C1351.

Kim et al. 1988 IgG from patients with Lambert–Eaton Syndrome blocks voltage–dependent calcium channels. Science 239: 405–8.

Dubel et al. Jun. 1992. Molecular cloning of the α–1 subunit of an ω–conotoxin–sensitive calcium channel, Proc Natl. Acad. Sci 89: 5058–62.

Appel, et al., "Amyotrophic Lateral Sclerosis: Associated Clinical Disorders and Immunologic Evaluations," 43 Arch. Neurol. 234–38 (1986).

Younger, et al., "Motor Neuron Disease and Amyotrophic Lateral Sclerosis: Relation of High CSF Protein Content to Paraproteinemia and Clinical Syndromes," 40 Neurol. 595–99 (1990).

Meininger, et al., "Serum Monoclonal Immunoglobulins in Amyotrophic Lateral Sclerosis: A Quantitative Analysis Using a New Western Blot Technique," 40 Neurol. 183(suppl 1) (1990).

Oldstone, et al., "Evidence For Immune–Complex Formation in Patients With Amyotrophic Lateral Sclerosis," 2 Lancet 169–72 (1976).

Palo, et al., "Kidney and Skin Biopsy in Amyotrophic Lateral Sclerosis," 1 Lancet 1270 (1978).

(List continued on next page.)

*Primary Examiner*—Marian C. Knode
*Assistant Examiner*—James L. Grun
*Attorney, Agent, or Firm*—Darby & Darby

[57] ABSTRACT

A method and kit are described that are useful in the diagnosis of amyotrophic lateral sclerosis or the evaluation of its progression. According to the method, a purified voltage-sensitive calcium channel complex is contacted with a biological fluid obtained from a person suspected of having, or known to have, amyotrophic lateral sclerosis. The voltage-sensitive calcium channel is of a type that ALS sera selectively reacts with. The reaction takes place for a time and under conditions sufficient for the calcium channel complex and anti-calcium channel complex antibodies that may be present in the biological fluid to form an antigen/antibody complex. The presence or absence of the antigen/antibody complex is then determined.

11 Claims, 12 Drawing Sheets

OTHER PUBLICATIONS

Engelhardt, et al., "Motor Neuron Destruction in Guinea Pigs Immunized With Bovine Spinal Cord Ventral Horn Homogenate: Experimental Autoimmune Gray Matter Disease," 27 J. Neuroimmunol. 21–31 (1990).

Horwich, et al., "Amyotrophic Lateral Sclerosis Sera Applied to Cultured Motor Neurons," 30 Arch. Neurol. 332–33 (1974).

Touzeau, et al., "ALS Serum Has No Effect on Three Enzymatic Activities In Cultured Human Spinal Cord Neurons," 36 Neuro. 573–76 (1986).

Hauser, et al., "Immunoblot Analysis of Circulating Antibodies Against Muscle Proteins in Amyotrophic Lateral Sclerosis and Other Neurologic Diseases," 36 Neurol. 1614–18 (1986).

Ordoñez, et al., "Antibodies Against Fetal Muscle Proteins in Serum From Patients With Amyotrophic Lateral Sclerosis," 39 Neurol. 683–86 (1989).

Ingvar–Maeder, et al., "Search for Antibodies to Skeletal Muscle Proteins in Amyotrophic Lateral Sclerosis," 74 Arch. Neurol. Scand. 218–23 (1986).

Endo, et al., "Antibodies to Glycosphingolipids in Patients With Multiple Sclerosis and SLE," 132 J. Immunol. 1793–97 (1984).

Pestronk, et al., "Patterns of Serum IgM Antibodies to GM1 and GD1a Gangliosides in ALS," 25 Ann. Neurol. 98–102 (1989).

Stefansson, et al., "Circulating Autoantibodies to the 200, 000–Dalton Protein of Neurofilaments in the Serum of Healthy Individuals," 228 Sci. 1117–1119 (1985).

Engelhardt, et al., "Experimental Autoimmune Motoneuron Disease," 26 Ann. Neurol. 368–76 (1989).

Tajti,et al., "Cyclophosphamide Alters the Clinical and Pathological Expression of Experimental Autoimmune Gray Matter Disease," 34 J. Neuroimmunol. 143–51 (1991).

Hamilton, et al., "Subunit Composition of the Purified Dihydropyridine Binding Protein From Skeletal Muscle," 28 Biochem. 7820–28 (1989).

Chang, et al., "A Combined Non–Denaturing and Denaturing Gel Electrophoretic Analysis of the Subunit Composition of a Membrane Protein: The Skeletal Muscle L–Type Calcium Channel," 172 Biochem. Biophys. Res. Comm. 751–58 (1990).

Ahlijanian, et al., "Subunit Structure and Localization of Dihydropyridine–Sensitive Calcium Channels in Mammalian Brain, Spinal Cord, and Retina," 4 Neuron 819–32 (1990).

Hofmann, et al., "The Molecular Structure and Regulation of Muscular Calcium Channels," 31 Curr Top Cell Regul 223–239 (1990).

Lacerda, et al., "Normalization of Current Kinetics By Interaction Between the$\alpha_1$ and $\beta$ Subunits of the Skeletal Muscle Dihydropyridine–Sensitive $Ca^{2+}$ Channel," 352 Nature 527–30 (1991).

Birnbaumer, et al., "Molecular Diversity and Function of G Proteins and Calcium Channels," 44 Biol. Reproduction 207–24 (1991).

Hui, et al., "Molecular Cloning of Multiple Subtypes of a Novel Rat Brain Isoform of the$\alpha_1$ Subunit of the Voltage–Dependent Calcium Channel," 7 Neuron 35–44 (1991).

Sieber, et al., "The 165–K Da Peptide of the Purified Skeletal Muscle Dihydropyridine Receptor Contains the Known Regulatory Sites of the Calcium Channel," 167 Eur. J. Biochem. 117–122 (1987).

Snowman, et al., "Anti–w–Conotoxin GVIA Antibodies: A Valuable Tool for the Identification of the Conotoxin Receptor of Rat Brain," 17 Soc. Neurosci. Abstr. 341 (No. 142.1 1991).

Tanabe, et al., "Primary Structure of the Receptor for Calcium Channel Blockers from Skeletal Muscle," 328 Nature 313–18 (1987).

Perez–Reyes, et al., "Induction of Calcium Currents By the Expression of the$\alpha$1–Subunit of the Dihydropyridine Receptor From Skeletal Muscle," 340 Nature 233–36 (1989).

Appel, et al., "A Rating Scale for Amyotrophic Lateral Sclerosis: Description and Preliminary Experience," 22 Ann. Neurol. 328–33 (1987).

Catterall, et al., "Molecular Properties of Dihydropyridine–Sensitive Calcium Channels in Skeletal Muscle," 263 J. Biol. Chem. 3535–3538 (1988).

Engel, et al., "Motor Nerve Terminal Calcium Channels in Lambert–Eaton Myasthenic Syndrome: Morphologic Evidence for Depletion and that the Depletion is Mediated by Autoantibodies," 560 Ann NY Acad Sci 278–90 (1989).

Imagawa, et al., "Purified Ryanodine Receptor From Skeletal Muscle Sarcoplasmic Reticulum is the $Ca^{2+}$ –Permeable Pore of the Calcium Release Channel," 262 J. Biol. Chem. 16636–43 (1987).

Lang, et al., "The Effect of Myasthenic Syndrome Antibody on Presynaptic Calcium Channels in the Mouse," 390 J. Physiol. 257–70 (1987).

Mintz, et al., "Inhibition of N–and L–Type $Ca^{2+}$ Channels by the Spider Venom Toxin $\omega$ AGA–IIIA,"88 Proc. Natl. Acad. Sci. USA 6628–31 (1991).

Morton, et al., "The $\alpha$1 and $\alpha$2 Polypeptides of the Dihydropyridine–Sensitive Calcium Channel Differ in Developmental Expression and Tissue Distribution," 2 Neuron 1499–1506 (1989).

Nagayama, et al., "Binding Domains of Stimulatory and Inhibitory Thyrotropin (TSG) Receptor Autoantibodies Determined With Chimeric TSG–Lutropin/Chorionic Gonadatropin Receptor," 88 J. Clin. Invest. 336–40 (1991).

Norman, et al., "Monoclonal Antibodies Against Calcium Channels," 560 Ann. NY. Acad. Sci. 258–68 (1989).

Sakamoto, et al., "Isolation and Biochemical Characterization of the Rabbit Brain $\omega$–Conotoxin GVIA Receptor," 34 Physiologist 109 (1991).

Vincent, et al., "Autoimmunity to the Voltage–Gated Calcium Channel Underlies the Lambert–Eaton Myasthenic Syndrome, A Paraneoplastic Disorder," 12 Trends Neurosci. 496–502 (1989).

Westenbroek, et al., "Clustering L–Type $Ca^{2+}$ Channels At the Base of Major Dendrites in Hippocampal Pyramidal Neurons," 347 Nature 281–84 (1990).

Appel, et al., "Amyotrophic Lateral Sclerosis: Etiology and Pathogenesis," *Current Neurology,* 287–310 (1991).

Appel, et al., "Immunoglobins from Animal Models of Motor Neuron Disease and From Human Amyotrophic Lateral Sclerosis Patients Passively Transfer Physiological Abnormalities to the Neuromuscular Junction," 88 Proc. Natl. Acad. Sci. USA 647–51 (1991).

Smith, et al., "Alterations in Dihydropyridine Receptor Binding Kinetics in Amyotrophic Lateral Sclerosis (ALS) Skeletal Muscle," 17 Soc. Neurosci. 1451 (Abstract 574.14 1991).

Engelhardt, et al., "Immune–Mediated Models of Motor Neuron Destruction in the Guinea Pig," 56 Adv. Neurol. 369–379 (1991).

Robitaille, et al., "Strategic Location of Calcium Channels At Transmitter Release Sites of Frog Neuromuscular Synapses," 5 Neuron, 773–79 (1990).

Troost, et al., "Lymphocytic Infiltration in the Spinal Cord of Patients With Amyotrophic Lateral Sclerosis," 8 Clin. Neuropathol. 289–294 (1989).

Williams, et al., "Motor Neuron Disease (Amyotrophic Lateral Sclerosis)," 66 Mayo Clin. Proc. 54–82 (1991).

Engelhardt, et al., "IgG Reactivity in the Spinal Cord and Motor Cortex in Amyotrophic Lateral Sclerosis, "47 Arch. Neurol. 1210–16 (1990).

Appel, et al., "Immunological Models of Amyotrophic Lateral Sclerosis," New Evidence in MND/ALS Research, Chap. 27, 189–96 (1991).

McEnery, M., et al., "Purified ω–Conotoxin GVIA Receptor of Rat Brain Resembles a Dihydropyridine–Sensitive L–Type Calcium Channel," 88(24) Proc. Natl. Acad. Sci. USA 11095–11099 (1991).

Delbono, et al., Immunoglobulins G (IgG) From Patients with Amyotrophic Lateral Sclerosis (ALS) Affect Dyhidropyridine Sensitive Calcium Channels of Skeletal Muscle, 59 Biophysical J1. 65a (1991).

Delbono, et al., "Calcium Current and Charge Movement of Mammalian Muscle: Action of Amyotrophic Lateral Sclerosis Immunoglobulins," 444 J1. Physiology 723–42 (1991).

Appel, et al., "Autoimmunity and ALS: A Comparison of Animal Models of Immune–Mediated Motor Neuron Destruction and Human ALS," 56 Adv. in Neurology 405–12 (1991).

FIG. 9

| ALS IgG (#) | ELISA<br>% Blockade of $\alpha_1$mAb-$Ca^{++}$Channel Binding by ALS IgG Preincubation | IMMUNOBLOT<br>Direct ALS IgG Binding to $Ca^{++}$ Channel $\alpha_1$ Subunit | IMMUNOBLOT<br>Blockade of $Ca^{++}$ Channel $\alpha_1$ Subunit-$\alpha_1$mAb Binding by ALS IgG Preincubation |
|---|---|---|---|
| 1 | 100± 1 (3)† | ++ | ++ |
| 2 | 100± 1 (3) | + | ++ |
| 3 | 81± 4 (10) | ++ | ++ |
| 4 | 80± 7 (3) | + | ++ |
| 5 | 68± 8 (3) | n.d. | n.d. |
| 6 | 48± 4 (3) | n.d. | n.d. |
| 7 | 40± 9 (3) | - | ++ |
| 8 | 32±11 (3) | + | ++ |
| 9 | 26± 7 (3) | +/- | + |
| 10 | 8± 4 (4) | + | - |
| 11 | 5± 4 (3) | - | - |
| 12 | 1± 2 (3) | - | - |
| 13 | 1± 1 (3) | - | - |

METHOD FOR DIAGNOSING AMYOTROPHIC LATERAL SCLEROSIS

This is a continuation of application Ser. No. 07/897,893, filed Jun. 12, 1992, now abandoned.

FIELD OF THE INVENTION

This invention relates to the diagnosis of amyotrophic lateral sclerosis.

BACKGROUND OF THE INVENTION

Amyotrophic lateral sclerosis (ALS) is a relentlessly progressive neurodegenerative disease of unknown etiology. (Charcot 1877; Mulder et al. 1969; Appel et al. 1986; Rowland 1984) Its major effect is the compromise of both upper and lower motoneurons, and while it spares the intellect, it produces irreversibly progressive weakness and paralysis, culminating in respiratory failure and death. Numerous studies attempting to implicate viruses, toxins (especially excitotoxins), and loss of trophic influences in ALS have provided, at best, weak circumstantial evidence. (Rowland 1984; Williams et al. 1991) While a genetic etiology has been described for ALS, familial ALS accounts for less than 10% of diagnosed cases. (Siddique et al. 1991; Mulder et al. 1986)

Autoimmunity has more recently been implicated in the causation of sporadic cases of ALS. Clinical studies supporting such a potential role for autoimmunity include both an increased incidence of autoimmune disorders in ALS patients 1877) and an increased incidence of paraproteinemias. Younger et al. 1990;

Meininger et al. 1990) Numerous reports have documented the presence of circulating or deposited immune complexes in ALS patients. (Oldstone et al. 1976; Palo et al. 1978) Post-mortem microscopic analysis of ALS tissues reveals the presence of IgG within upper and lower motoneurons, and the presence of inflammatory foci of T-cells and reactive microglia within the spinal cord ventral horn. (Engelhardt et al. 1990) Direct investigations have failed, however, to confirm the role of humoral autoimmunity in tissue culture (Horwich et al. 1974; Touzeau et al. 1986), and have failed to confirm reactivity of IgG against various antigens using immunoblot techniques. (Hauser et al. 1986; Ordonez et al. 1989) Further, these investigations have not defined the presence of antibodies against "novel growth factors" (e.g., glucose-6-phosphate isomerase), thought by some to be decreased in ALS (Chaput et al. 1988; Ingvar-Marden et al. 1986), and have failed to demonstrate sensitivity and specificity of anti-ganglioside and neurofilament antibodies reported in some patients with ALS. (Endo et al. 1984; Pestronk et al. 1989;

Stefansson et al. 1985)

An alternative approach providing evidence for autoimmunity in ALS has been the development in guinea pigs of two distinct models of immune-mediated motoneuron disease: experimental autoimmune motoneuron disease (EAMND), and experimental autoimmune gray matter disease (EAGMD). EAMND (Engelhardt et al. 1989) is a purely lower motoneuron syndrome induced by monthly injections of purified bovine spinal cord motoneuron. EAGMD (Engelhardt et al. 1990) is produced after a single inoculation of spinal cord ventral horn homogenate, and like human ALS, produces a progressive compromise of both upper and lower motoneurons with associated clinical symptoms, IgG staining intracellularly in upper and lower motoneurons and inflammatory foci within spinal cord ventral horns. Further, EAGMD can be prevented with pretreatment or early post-treatment with cyclophosphamide. (Tajti et al. 1991)

Additional evidence for autoimmunity in the animal models is the ability of immunoglobulins from affected guinea pigs to passively transfer physiological abnormalities of the neuromuscular junction into mice. Following the globulin injections, there is an increase in miniature end plate potential (MEPP) frequency, with normal MEPP amplitude, decay time constant, and resting membrane potential. Similar passive transfer experiments using human immunoglobulins also demonstrate an increased MEPP frequency.

ALS, however, is frequently misdiagnosed by general medical doctors and even by neurologists. Lack of knowledge of the disease's etiology has inhibited development of a simple and effective diagnostic. The diagnosis depends upon evidence of progressive proximal and distal extremity weakness accompanied by electrical and morphologic evidence of denervation. However neuropathies, myoneural junction abnormalties and other neuromuscular disorders must be ruled out. Similarly, predicting the rate of progression of ALS, once it has been identified, is difficult. Thus, there exists a need for an improved test for the diagnosis of ALS.

SUMMARY OF THE INVENTION

The present invention relates, in one aspect, to an improvement in a procedure for diagnosis of amyotrophic lateral sclerosis, or the evaluation of the progression of that disease. The improvement involves determining, in an immunoassay, the presence in a biological fluid obtained from person having ALS of antibodies that selectively react, or cross-react, with the alpha$_1$ subunit of L-type skeletal muscle calcium channel. In another aspect of the invention, purified L-type skeletal muscle calcium channel is contacted with a biological fluid obtained from an individual having ALS. The reaction takes place for a time and under conditions sufficient for the channel and anti-channel antibodies to form an antigen/antibody complex. The presence or absence of the complex is then determined in order to aid in ALS diagnosis or prognosis. In another aspect, the invention involves a method for determining ALS specific antibodies from a biological fluid obtained from an individual having ALS. The method comprises the steps of providing the ALS specific antibodies; selectively insolubilizing said ALS specific antibodies by an antibody/antigen reaction; determining the presence or absence of insolubilized ALS specific antibodies by means of a detectable label; and correlating the presence or absence of said detectable label with the presence or absence of the ALS specific antibodies.

BRIEF DESCRIPTION OF THE DRAWINGS

In FIG. 2A human cytoskeletal proteins (enriched in 160 Kd and 200 Kd neurofilament) were precipitated onto microtiter wells of final concentration of 10 $\mu$g/ml. In FIGS. 2A and 2B "other MND" refers to other motoneuron disease, "NC" refers to a normal control, "−ADC" refers to a non-autoimmune neurological disease control, and "+ADC" refers to an autoimmune neurologic disease control. Presence of plated neurofilament was confirmed by assay using monoclonal antibodies directed against the 160 Kd and 200 Kd species. In FIG. 2B, 0.6M KCl soluble cytoplasmic proteins were plated at a final concentration of 10 $\mu$g/ml. For ELISAs depicted in this figure, human sera were diluted 1:1,250 prior to testing. Each point represents the mean value for colored alkaline phosphatase product measured at $OD_{405}$ in triplicate samples after 2 hours at 37° C.

In FIG. 4A, data for the rates of disease progression (units change in Baylor ALS function scores per month), available for 38 of 48 patients tested in ELISA (see FIG. 2), are plotted as a function of their ELISA reaction product values (measured at $OD_{405}$). The line represents the least squares regression analysis for depicted data (adjusted $r^2$=0.8). In FIG. 4B, the box and whisker diagram depicts the same data as presented in FIG. 4A, after grouping of ALS patients into populations based on their reactions of ELISA. Populations 1 and 2 represent those patients whose ELISA reactions were respectively, either less than (1) one or greater than (2) two standard deviations above control ELISA reaction values. These populations are plotted as a function of disease progression rate (numbered axis) where the enclosed boxes represent population 25th through 75th quartiles, the cross hatch within each box represents the population median, and each small vertical line above the population range markers define individual patient disease progression rates for each population.

FIG. 8A shows inhibition by ALS IgG of an anti-$\alpha_1$ subunit directed mAb binding to purified L-type voltage dependent calcium channel. FIG. 8B reveals lack of such reactivity upon testing an anti-β subunit directed mAb. FIG. 8C documents the lack of ALS IgG produced inhibition of cytoplasmic epitope-directed anti-$\alpha_1$ antibody binding.

FIG. 9 is a summary of ELISA and immunoblot reactivity for tested ALS IgGs. Dagger refers to the number of experiments performed for each IgG.

DETAILED DESCRIPTION

Figure 1:
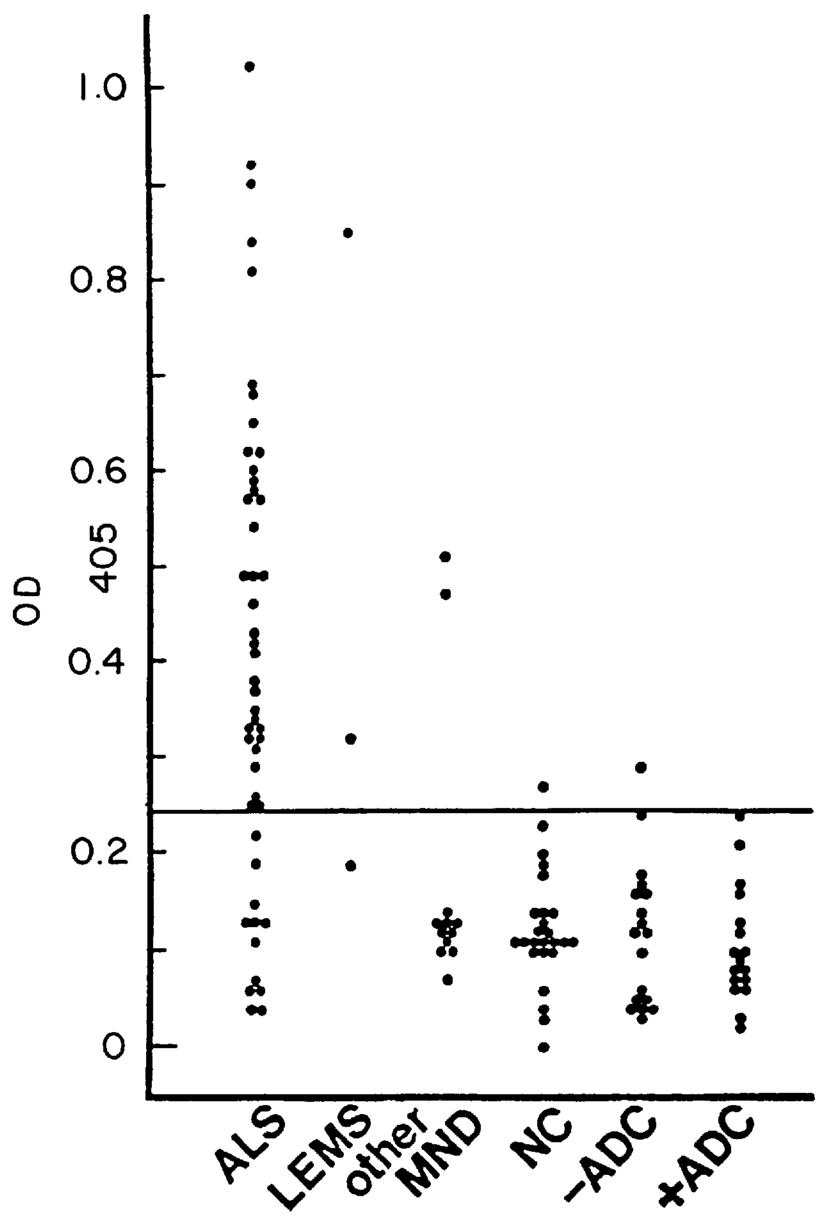
FIG. 1 is a graph depicting a quantitative comparison of human serum binding to skeletal muscle L-type calcium channels. Results are of ELISA for individual citrate-treated sera tested against purified L-type calcium channel. Sera were diluted 1:1,250 prior to ELISA addition. Mean values of individual sera, tested at $OD_{405}$ in duplicate and repeated in 3 experiments, are depicted after 3 hours incubation at 37° C., followed by 15 hours incubation at 25° C. The bar shown defines a value 2 standard deviations above pooled control means.

We have determined that antibody containing fluids from ALS patients react with purified calcium channel protein in a sensitive and specific fashion. The formation of complexes between antibodies and the channel proteins can be detected in order to obtain information for the diagnosis of ALS, or its rate of progression.

Any means for determining the formation of antigen/antibody complexes may be used to practice the invention, including Western Blot, radioimmunoassay, or ELISA methods. The method used may be either direct or competitive (i.e. determining the presence of the complex directly, or through competitive inhibition with another antibody). The preferred embodiment of the invention is a direct assay, although a competitive assay may have potential for high sensitivity. Many methods and variations for determining the presence of the complex between the calcium channel and antibody thereto will be apparent to one skilled in the art.

A typical suitable immunoblot technique begins with separation of highly purified calcium channel by SDS gel electrophoresis. The purified channel is then blotted onto suitable paper, such as polyvinylidine difluoride or nitrocellulose, and reacted with sample immunoglobulin. Retained antibodies can be identified by reaction with labeled anti-human antibody followed by detection of the label.

A suitable immunoassay can be performed wherein purified calcium channel, absorbed onto a polystyrene support, is contacted with serum from a person suspected of having ALS. The mixture is maintained under conditions and for a time whereby a detectable complex forms between antibody to calcium channel and the calcium channels. The complex can then be detected, for example, by determining the presence of human antibody using a labeled anti-human antibody. A stepwise procedure is preferred.

In a competitive immunoassay, a monoclonal antibody for the $\alpha_1$ subunit of purified calcium channel competitively inhibits, or is competitively inhibited by, the binding of ALS antibodies. For example, in a procedure described below, inhibition by ALS sera of the binding of a monoclonal antibody to calcium channel is determined using a labeled antibody against the monoclonal antibody.

Many variations on these procedures are possible. For example, instead of adding anti-human antibody, a labeled antigen which is bound by divalent anti-calcium channel antibody can be employed. Such labeled antigens include labeled $\alpha_1$ subunit, or a labeled peptide coding for an antigenic part of the $\alpha_1$ subunit. These reagents are further discussed below.

Suitable wash steps should be employed. For example in the stepwise immunoassay procedure described above, unbound serum can be washed away following incubation of patient serum with purified calcium channels, and unbound labeled anti-human antibody washed away in a later step. Suitable washing agents and procedures are well known.

Examples of suitable detectable labels include enzymes (such as horseradish peroxidase), radioactive tags, and fluorescent tags. Chemiluminescent techniques can be employed. Biotin affinity, or other affinity, labeling techniques may also be used. For example in the embodiments described above, biotin labeled anti-human antibody may be employed and a labeled biotin binding moiety, such as enzyme labeled avidin, streptavidin, or anti-biotin, can be added and the presence of the label determined.

The calcium channel, or an effective antigenic part of the channel, is preferably made insoluble, for example by coating on a solid support. Examples of suitable solid supports include microtiter plates, beads, sheets and pads. The support may consist of polystyrene, or any other suitable material. The antigenic material coated on the solid support may be attached via physical absorption or by covalent means, so long as normal washing procedures do not remove it.

Preferably the purified calcium channel is a purified L-type calcium channel, most preferably from skeletal muscle. The L-type voltage-sensitive calcium channel is a gated ionophore which regulates calcium entry into cells. It consists of several membrane-spanning subunits and closely associated intra- or extra-cellularly directed subunits, that are collectively found in a variety of tissues, including muscle, ventral spinal cord, and brain. (Hamilton et al. 1989; Chang et al. 1990; Ahlijanian et al. 1990; Hofmann et al. 1990) The alpha$_1$ subunit forms the primary calcium ion selective pore, which is modified in its actions by several other species of protein, both directly attached as subunits (Lacerda et al. 1991), or available for limited interactions, like G-proteins. (Birnbaumer et al. 1991) The invention, however, can be used in determining complexes that are selectively formed between ALS patient antibodies and any type of purified calcium channel. For example, we have also determined the presence of antibodies in ALS sera to brain N-type voltage-sensitive calcium channels. The testing of purified calcium channel for selective reactivity with ALS sera is described below.

Without wishing to be bound by any theory of the invention, our findings suggest that antibodies from ALS patients may recognize similar epitopes on N-type channels and L-type channels. Similarities in structure between N-type, skeletal muscle L-type and brain L-type channels have been reported (Hui et al. 1991; Dubel et al. 1992) suggesting structural bases for such immunoglobin cross reactivity.

Purified muscle L-type calcium channel for use in the invention can be obtained according to the method of Schneider et al. as modified from Sieber et al. 1987. It is not necessary for all methods that the purified L-type calcium channel be highly purified, although with some techniques we have obtained better results using highly purified antigen. For example in a competitive assay only partially purified calcium channel can be used if desired. Highly purified calcium channel is preferred in direct assays.

Methods for the purification of natural brain (i.e. central) N-type calcium channel has been described by Snyder et al. Recombinant production of desired N-type channel based antigens can be carried out based on the known sequence of N-type channels.

A direct electrophysiological test shows that ALS IgG alters calcium entry into cells. An interaction of ALS IgG with these L-type calcium channels can be demonstrated, with decreases noted in calcium current peak amplitude and in charge movement.

A part of the calcium channel which reacts with antibody from the biological fluid tested may be employed in the method of the invention, as opposed to the entire channel. We have determined, by immunoblot study, that the $\alpha_1$ subunit of the L-type calcium channel contains an epitope(s) for which ALS patient antibodies are specific. Thus, purified $\alpha_1$ subunit can be employed to complex with antibody in ALS patient sera in the method of the invention. The $\alpha_1$ subunit has a molecular weight of about 170 kD, and a known sequence as described in Tanabe et al. 1987 and Perez-Reyes et al. 1989. The $\alpha_1$ subunit can be partially separated from other subunits by preparative isoeletric focusing (BIORAD), though more complete separation is achieved by preparative SDS electrophoresis (BIORAD). While the latter method has the disadvantage of denaturing this subunit, at least some antibodies present in ALS sera react with the denatured protein, as evidenced by immunoblot of SDS gels.

Of course, any purified antigen that is immunologically cross-reactive with a purified voltage-sensitive calcium channel that is useful in the invention can be used in its place, as long as it also selectively reacts with ALS sera.

For example, a polypeptide of the $\alpha_1$ subunit which effectively presents an epitope recognized by ALS patient antibodies can be employed in the method of the invention.

Any antibody containing fluid may be used to provide the calcium channel binding antibody, including whole blood, serum, plasma, urine, lacrimal fluid or saliva. Serum is preferred. Purified immunoglobulins may be used, and may provide more accurate differentiation between ALS and non-ALS samples.

The method need not result in a certain diagnosis of ALS. We have determined, for example, that the sera of patients with Lambert-Eaton myasthenic syndrome may contain antibodies that bind to L-type calcium channels. Such sera, used in the method of the invention, may result in a positive result without indicating ALS ("false positives"). The method also need not be used for diagnosis of all forms of ALS. Familial ALS, for example, might not be determinable using the method.

As noted above, a direct assay is preferred. If desired, however, monoclonal antibodies for use in a competitive assay can be obtained, for example, by immunizing mice with purified calcium channel, and screening hybridomas produced therefrom by immunoblot for reactivity with the desired subunit of the calcium channel. Anti-$\alpha_1$ subunit antibodies obtained can be tested for selective inhibition of ALS antibodies with immobilized calcium channel. Anti-$\beta$ subunit antibodies, obtained by this or another method, might be used in a competitive assay to distinguish ALS antibodies (which we believe include no anti- $\beta$ subunit antibodies) from, for example, Lambert-Eaton antibodies (which our preliminary data indicate include both anti-$\alpha$ and anti-$\beta$ subunit antibodies). The presence of anti-$\beta$ subunit antibodies can also, of course, be determined using a direct immunoblot assay, which requires no competing anti-$\beta$ subunit monoclonal antibodies.

In another aspect of the invention, a kit is provided for the diagnosis of ALS. The kit includes a purified antigen that is selective for ALS patient antibodies. The antigen may be purified $\alpha_1$ subunit of L-type voltage-sensitive calcium channel, preferably skeletal muscle L-type calcium channel. The antigen may also be purified central N-type calcium channel. Purified antigens that are immunologically cross-reactive with those subunits or channel, and that are selective for ALS sera, can also be used in the kit. The purified antigen can be coated on a solid support. Also included in the kit are means for detecting the formation of a complex between the L-type calcium channel complexes and anti-calcium channel complex antibodies.

This invention is further illustrated by the experiments set forth below. The description of these experiments is intended to exemplify, and not limit, the scope of the invention.

First Set of Experiments

METHODS

Patient serum and immunoglobulin preparation

Blood was collected in hospital and clinic settings from randomly selected patients and volunteer controls who had fasted for the previous 8–12 hours. Following phlebotomy, blood samples were centrifuged at 1500xg for 10 minutes, and cell-free supernatants underwent a second centrifugation at 10,000xg for 20 minutes. 10% v/v sodium citrate buffer (pH 5: final concentration 0.1 M) was added with end over end mixing for 24 hours at 4° C. After an additional 10,000xg centrifugation to remove cryoprecipitate and other precipitated proteins, supernatants were equilibrated to pH 7.4, and aliquoted for storage at −80° C. until needed.

Human immunoglobulins used in ELISAs were typically prepared from either citrate treated serum or plasma, using a combination of 45% ammonium sulfate precipitation and high flow rate ion exchange chromatography. Following ammonium sulfate fractionation, a resuspended and dialyzed sample was applied to a ZetaPrep cation exchange cartridge (CUNO) at flow rates of 5–50 ml/min (depending on cartridge size), in 0.02 M acetate buffer (pH 5.6). Following extensive washing, sample was eluted through an anion exchange cartridge with 0.08 M tris buffer (pH 8.0). Typical immunoglobulin purities of at least 90% were obtained by this method.

Protein A-agarose affinity chromatography was used to provide a final purification step for some ALS IgGs. However, previous experience with cross-contamination of samples by this method necessitated the use of previously unused affinity matrix for the purification of each patient sample.

Determination of total IgG concentrations in human sera was performed on a Technicon RA 1000 system analyzer (Technicon), using a turbidometric method that measures the amount of tubidity produced by immune complex formation between serum IgG and human IgG antiserum. Polyethylene glycol was used to accelerate IgG antigen-antibody complexes, which were assayed at 340 nm.

Antigen purification

Skeletal muscle dihydropyridine-sensitive L-type voltage-gated calcium channel complexes were obtained from several laboratories, with several different degrees of final purification. Partially purified channel complexes were prepared following previously described methods. Purifications were taken through low pressure anion exchange chromatography prior to testing on ELISA. More highly purified skeletal muscle calcium channel protein (containing 1.7 nmol L-type channel/mg total protein) was obtained on a preparative scale using a slightly simplified procedure that incorporated HPLC ion exchange chromatography and a final sucrose gradient centrifugation step.

In addition to fractions specifically enriched in the L-type calcium channel, we prepared a cytosolic protein mixture depleted of dihydropyridine binding sites from skeletal muscle 0.6 M KCl supernatant fractions after initial centrifugation steps. Prior to use in assays, these fractions were extensively dialyzed with 50 mM Tris buffer (pH 7.4) containing 0.1 M NaCl, employing a 6–8000 molecular weight cut-off membrane. Cell membrane fractions partially depleted of L type channels (containing approximately 10% of total bound radiolabelled DHP ligand) were also obtained from rabbit skeletal muscle. After twice extracting membranes with a 4% digitonin solution to remove calcium channel complexes, these membranes were dialyzed with 10 mm MOPS buffer (pH 7.4), containing 0.1 M NaCl and 0.05% Tween 20 detergent, and briefly sonicated before use.

L-type calcium channels enriched for the B-subunit were prepared by adsorbing digitonin extracted membrane proteins to wheat germ agglutinin affinity matrix, and incubating the adsorbed proteins for 12 hours on ice with a buffer containing 4% CHAPS detergent and 10% glycerol. Dissassociated calcium channel subunits not adsorbed to the matrix were eluted, and next applied to a preparative isoelectric focusing apparatus (Bio-Rad), in pH 4–10 ampholines (SERVA). After isoelectric focusing, relevant fractions were removed for testing. $\alpha_2\delta$ subunit complex of the skeletal muscle calcium channel, as well as skeletal muscle ryanodine receptors, $Ca^{++}$ ATPase, and calsequestrin were purified per Hamilton et al. 1989; Hamilton et al. in press and Mclennan et al. 1971.

ELISA

Non-detergent-containing antigens were diluted in 0.1 M bicarbonate buffer (pH 8.4) to a final concentration of 1–3 μg protein/ml, prior to application to 96 well polystyrene ELISA plates (100 μl/μiter well:CORNING). Because digitonin (and to a lesser extent, CHAPS) in antigen micelles interfered with the rate and extent of protein binding to plastic, detergent-containing samples were allowed to plate for 48 hours at 4° C., while other antigens were added overnight at 4° C. Alternatively, antigen could be covalently linked to Cova-link ELISA plates (NUNC), reducing the time required for antigen binding. Binding site plating densities for L-type calcium channel antigen, as determined by dihydropyridine radioligand binding, were typically 2–4 fmol (in 0.125 μg) per μtiter well for partially purified preparations, and up to 20 fmol (in 0.013 μg) per μtiter well for highly purified material. Excess antigen was then removed by rinsing with a solution of 0.9% NaCl and 0.05% TWEEN 20 (saline/TWEEN), and wells were blocked for an additional 2 hours at 37° C. (for non-detergent bound antigens) or 48 hours at 4° C. (for detergent-containing antigens), using a 50 mM TRIS solution (pH 7.4) containing 1% BSA (fraction V, SIGMA), 0.9% NaCl and 0.05% TWEEN 20 detergent (blocking buffer; 250 μl/well).

Primary antibodies (human sera or immunoglobulin preparations) were added to antigen-coated wells for two hours at 37° C. Sera and IgGs were diluted in blocking buffer prior to addition; human IgGs were assayed at concentrations ranging from 0.05–200 μgs/ml (typically, 2–100 μg/ml), while sera were added at dilutions of 1:50–1:156,250 (typically, 1:250–1:6,250). After removal of unbound serum proteins by nine rinses with saline/TWEEN solution, a 1:2000 dilution of alkaline phosphatase-conjugated goat anti-human Fc-specific IgG (Sigma, Tago) (in blocking buffer) was next applied (100 μl/μtiter well:TAGO) for one hour at 37° C. Following further extensive rinsing in saline/TWEEN solution, 0.4 mg/ml para-nitrophenyl phosphate (PNPP: SIGMA) in 0.1 M sodium carbonate/lmM MnCl2 buffer (pH 9.5) was introduced to the wells (95 μl/μtiter well) and incubated at 37° C. At intervals after substrate addition, alkaline phosphatase activity was assayed spectrophotometrically at 405 nm to measure colored product formation (with plate background subtraction at 490 nm), using A Bio-Tek 8000 microplate reader with dual wavelength reading function.

The presence of antigenically intact, plated calcium channel antigen was verified for each 96 well plate by addition to some μtiter wells of serially diluted mouse monoclonal antibody to the gamma subunit of rabbit L-type channel. A goat anti-mouse alkaline phosphatase-conjugated immunoglobulin (Promega) diluted 1:1000 was used as a second antibody.

Non-specific binding of phosphatase-conjugated antibody, and the resultant colored product formation observed during 18 hour ELISA incubations, were minimized by blocking with highly purified albumin fractions. To quantitate the amount of non-specific binding still present, parallel binding assays were employed, using identical IgG fractions tested on blank BSA-blocked plates. Significant background reactions were noted in approximately 10% of IgG samples and 2–3% of serum samples tested, and were subtracted from values obtained using antigen-coated plates to provide specific channel binding data.

Likewise, potential direct contributions to colored product formation caused by human IgG fractions and non-specifically bound second antibody were tested by removal of either primary human IgG or alkaline phosphate conjugated second antibody, or examined after cleavage and removal of the Fc portion of selected primary antibodies (to which the second antibody was directed). No conversion of pNPP to colored reaction product was observed when any of these tests were performed.

Assessment of disease progression

All patients followed longitudinally in the Baylor ALS clinic underwent routine monthly or bimonthly comprehensive quantitative analyses of upper and lower motoneuron function. Scores defining the degree of motor disability for each patient were plotted as a function of time in months. Patients were included in this study when their change in disability score with time (disease progression) could be modelled by linear regression ($r^2$>0.9), and when sufficient data were available to plot such rates for a 6–12 month period surrounding serum collections used for these experiments. Patients taking immunosuppressants were excluded from this analysis.

RESULTS

L-Type Calcium Channel ELISA: Reactivity with patient sera

Sera from ALS patients demonstrated specific and sensitive binding of L-type calcium channel protein in ELISA. 48 ALS patient sera, randomly selected from clinic phlebotomy samples, were compared with sera from normal volunteers, patients with autoimmune diseases, patients with non-autoimmune neurologic disease, and non-ALS motoneuron disease patients at 1:1,250 dilution, and studied for reactivity against highly purified rabbit L-type calcium channel antigen (0.125 μg total protein/ml final plating concentration). Age, sex and disease type distributions for each group are described in Table 1.

TABLE 1

Clinical and Demographic Characteristics of Patients Tested by Serum ELISA*

| Population | Description | n | Total | Mean Age (± SEM) | Sex Ratio M/F % |
|---|---|---|---|---|---|
| ALS | Amyotrophic Lateral Sclerosis | | 48 | 51.8 ± 1.8 | 67/33 |
| LEMS | Lambert Eaton Myasthenic Syndrome | | 3 | 56.7 ± 11.9 | 100/0 |
| Other motoneuron disease | | | 12 | | |
| | Familial ALS | 7 | | 53.1 ± 2.1 | 67/33 |
| | Spinal muscular atrophy | 3 | | | |
| | Post-polio syndrome | 1 | | | |
| | Unidentified motoneuron disease | 1 | | | |
| Normal control | Volunteer | | 25 | 48.8 ± 2.7 | 60/40 |
| Non-autoimmune neuologic disease control | | | 18 | | |
| | Peripheral neuropathy | 4 | | 57.0 ± 4.0 | 67/33 |
| | Cerebrovascular accident / multi infarct state | 4 | | | |
| | Myelopathy | 2 | | | |
| | Radiculopathy | 1 | | | |
| | Charcot-Marie-Tooth | 1 | | | |
| | Vertigo | 2 | | | |
| | Arnold-Chiari malformation | 1 | | | |
| | Hereditary spastic paraparesis | 1 | | | |
| | Bulbar neuropathy | 1 | | | |
| | Tourette's | 1 | | | |
| Autoimmune neurologic disease control | | | 17 | | |
| | Multiple sclerosis | 5 | | 52.4 ± 5.0 | 47/53 |
| | Myasthenia gravis | 5 | | | |
| | Polymyositis | 3 | | | |
| | Rheumatoid arthritis vasculitis | 2 | | | |
| | Systemic lupus erythematosis | 1 | | | |
| | Paraneoplastic neuropathy | 1 | | | |

*P > 0.1 for comparison of ages

After 18 hours, most control sera reacted minimally to plastic-bound L-type calcium channel protein (FIG. 1). Control ELISA reaction values could be modelled as normal distributions, with almost identical control population means and standard errors (Table 2; note that the ALS population ELISA results did not distribute normally, and thus non-parametric statistical tests are used for all other statistical analyses).

TABLE 2

Human Serum Antibody Binding to L-type Skeletal Muscle Calcium Channel

| Population | Mean ± SEM | Median | n |
|---|---|---|---|
| ALS | 0.43 ± 0.04 | 0.38 | 48 |
| LEMS | 0.45 ± 0.20 | 0.32 | 3 |
| Other MND | 0.18 ± 0.04 | 0.13 | 12 |
| Normal control | 0.12 ± 0.01 | 0.11 | 25 |

TABLE 2-continued

Human Serum Antibody Binding to L-type Skeletal Muscle Calcium Channel

| Population | Mean ± SEM | Median | n |
|---|---|---|---|
| Non-autoimmune disease control | 0.12 ± 0.02 | 0.12 | 18 |
| Autoimmune disease control | 1.11 ± 0.02 | 0.09 | 17 |

When significant antigen binding was defined as that which produced levels of colored alkaline phosphatase reaction product greater than two standard deviations above mean values obtained for binding of sera from control patient populations, approximately 75% of ALS sera expressed significant binding to this antigen, while less than 5% of control patients appeared to bind significantly (FIG. 1). Most of the reactive ALS sera could be detected at dilutions of 1:6250–1:25,000.

Four additional patients also had sera which reacted strongly to the calcium channel antigen. These individuals included two of three patients with Lambert-Eaton myasthenic syndrome (LEMS), one patient with ALS-like motoneuron disease and protracted time course (>15 years), and one patient with clinical ALS and a family history of one first degree relative (brother) with ALS. However, patients with documented multi-generation familial ALS, post-polio syndrome, and spinal muscular atrophy patients with family pedigrees did not react in the ELISA assay. Neither did patients with recent CNS injury or chronic nervous system autoimmune disease react in this assay with the calcium channel antigen.

Figure 2A:
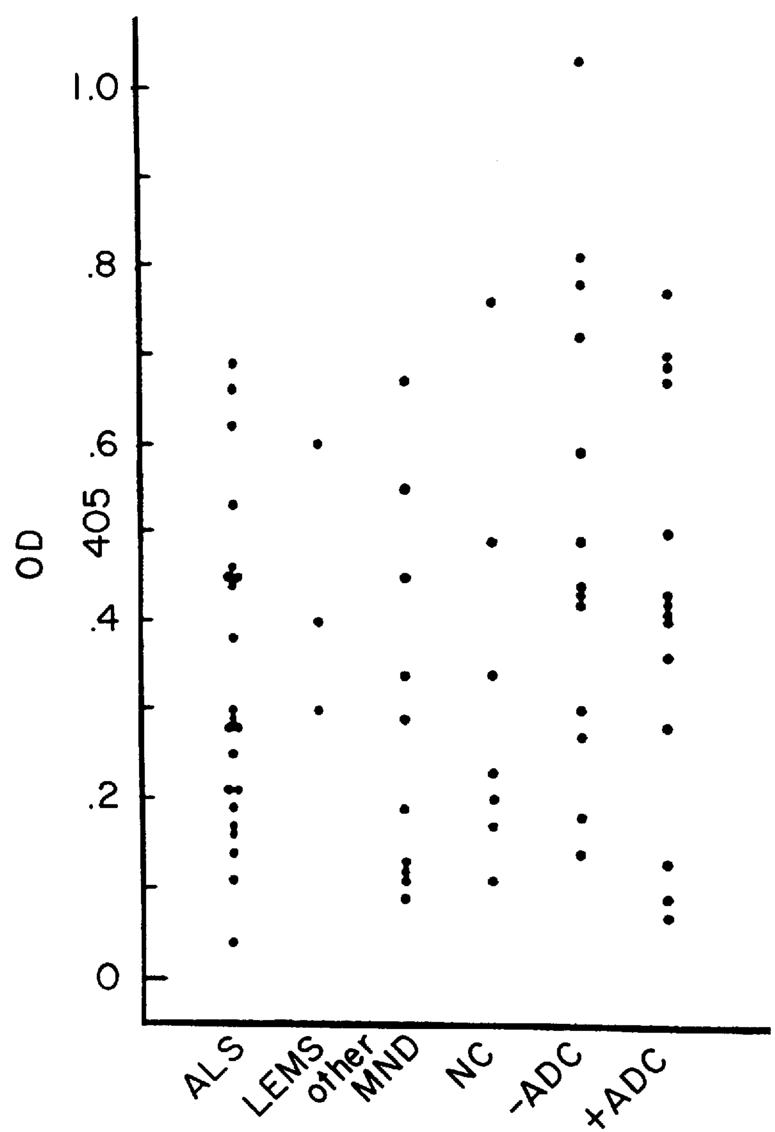
FIGS. 2A and 2B are graphs depicting quantitative comparisons of human serum binding to cytoskeletal and cytoplasmic proteins. Results were obtained from ELISA of some of the same sera used in FIG. 1 tested against either human brain derived cytoskeletal proteins (FIG. 2A), or rabbit skeletal muscle cytoplasmic proteins (FIG. 2B).
Figure 2B:
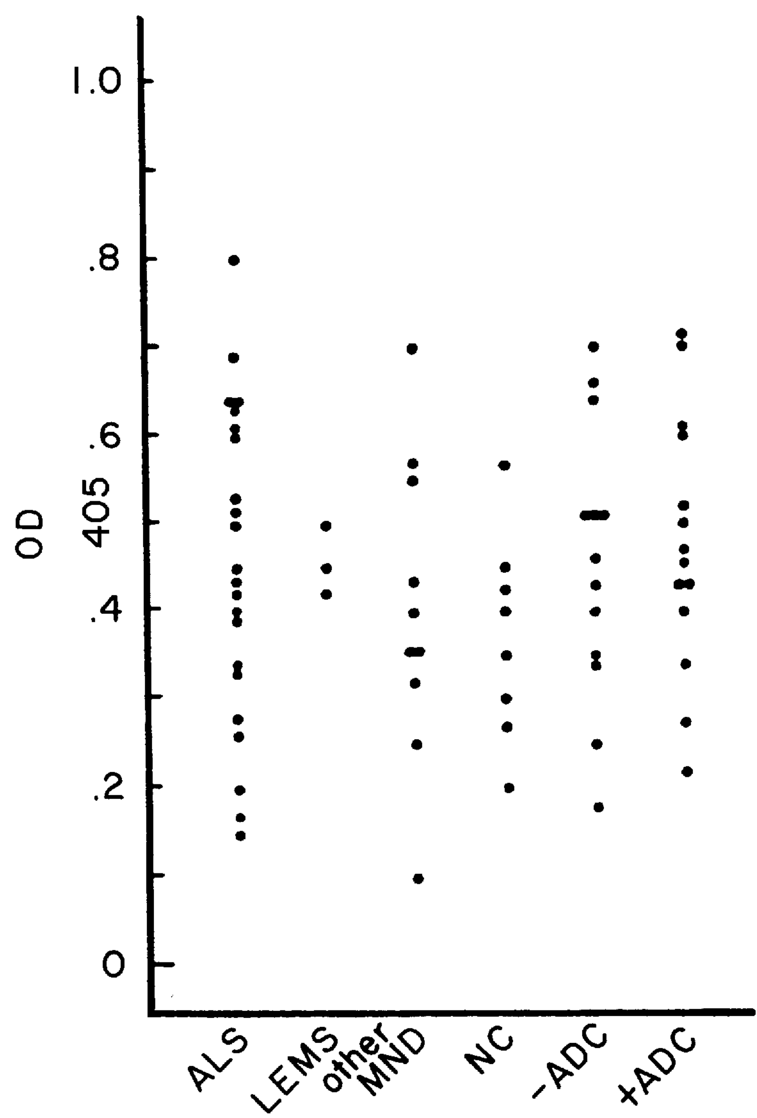

Sera from ALS patients could not be differentiated from other patients or controls with respect to binding to muscle cytosolic proteins or cytoskeletal proteins, or with respect to the presence or absence of anti-ganglioside antibodies. The lack of binding to cytosolic proteins and cytoskeletal proteins is demonstrated by the results shown in FIG. 2. Also, in data not shown, greater dilutions of human sera (up to 1:31,250) provided qualitatively similar results to those depicted in FIG. 2, when tested against cytoskeletal or cytoplasmic proteins, and serum titer curves against these antigens did not reveal greater binding by sera from ALS patients at any tested dilution. Further, major reductions in ALS serum binding were noted when detergent-extracted membrane fractions that were largely depleted of $^3$H-DHP-bound L-type calcium channel (see Methods section) were employed as antigen.

ELISA reactivity of ALS sera with calcium channel proteins was not simply a non-specific result of greater IgG levels in ALS patients relative to controls. Total IgG levels in sera from ALS patients ranged from 5–18 mg/ml, and were not significantly different from levels found in sera from patients with autoimmune diseases. Normalizing ELISA reactivity to a constant amount of IgG gave identically sensitive and specific results.

Interaction with purified patient immunoglobulins

Figure 3B:
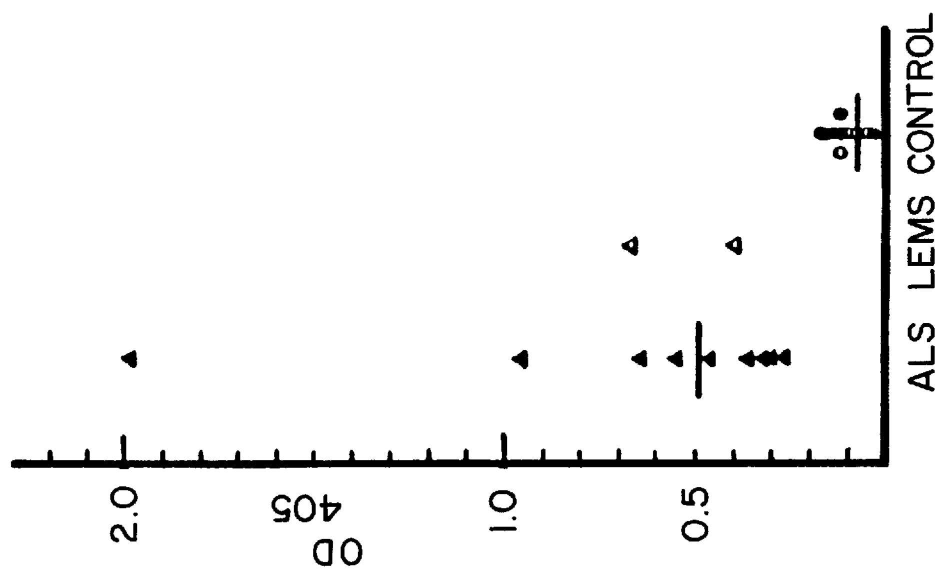
FIGS. 3A and 3B depict a quantitative comparison of human IgG binding to L-type skeletal muscle calcium channel. Purified immunoglobulins were added at a concentration of 5 $\mu$g/100 $\mu$l to microtiter wells pretreated either with partially purified (FIG. 3A) or highly purified (FIG. 3B) skeletal muscle L-type calcium channel. Depicted for each IgG tested are mean values of chromatic alkaline phosphatase reaction product, measured at $OD_{405}$ for triplicate samples in two experiments after 3 hours at 37° C. or 3 hours at 37° C., followed by 15 hours at 25° C. Bars define median values for ALS patient IgGs (▲), LEMS patient IgGs (Δ), normal control volunteer IgGs (○) and neurologic disease control patient IgGs (●).
Figure 3A:
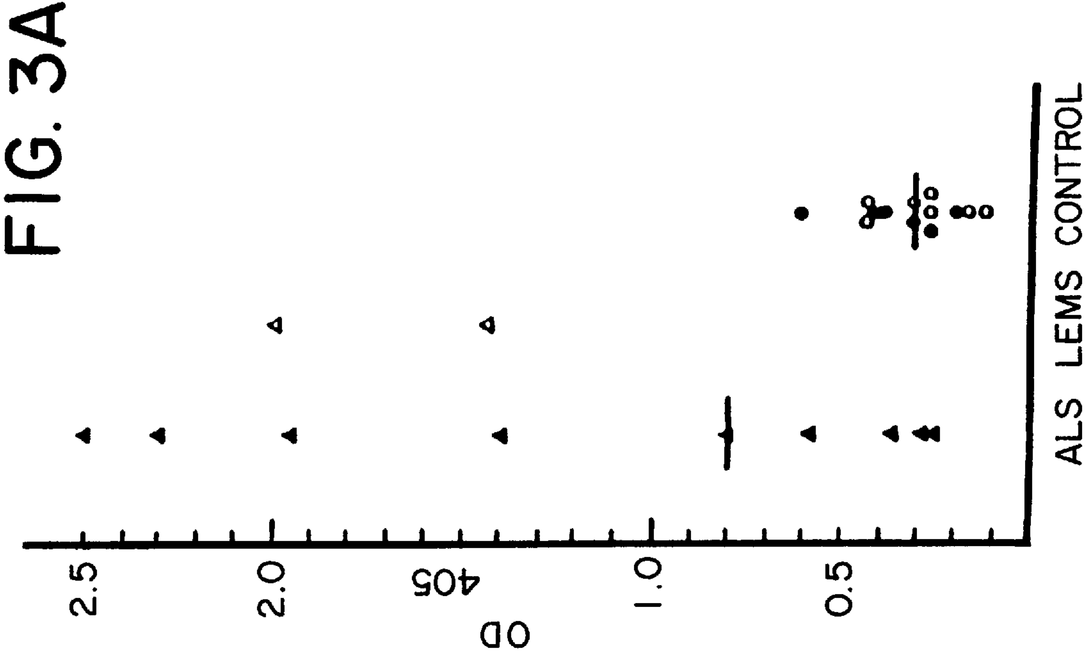

Immunoglobulins purified from ALS patients also bound to L-type calcium channel proteins. To demonstrate that ALS IgG behaved similarly to total serum fractions in ELISA, immunoglobulins derived from plasma or sera of normal volunteers, patients with other neurologic diseases, or ALS patients were added at equal concentrations to ELISA Plates pre-treated with either partially purified (4 fmol/$\mu$titer well plating concentration) or highly purified (20 fmol/$\mu$titer well plating concentration) digitonin-solubilized rabbit L-type calcium channel complexes. Subsequent alkaline phosphatase-based ELISA revealed binding of ALS patient IgGs to the partially purified plastic-bound calcium channel antigen, and differentiated the action of ALS IgG from that of all human normal control and most neurologic disease control IgGs (FIG. 3A; Wilcoxan rank-sum $|Z|<0.02$). IgG fractions from the two previously reactive patients with LEMS also reacted strongly in this assay. Separation of ALS and control immunoglobulin responses was more pronounced when highly purified calcium channel was used as antigen (FIG. 3B; two sample Wilcoxan z-statistic=3.97; $|z|<0.0001$). Reactivity of ALS immunoglobulins to L-type calcium channel antigen, however, was not qualitatively affected by the method of channel complex purification. Further, highly purified calcium channel gave similar rank orders for ALS and control patient ELISA responses.

As with sera, no differential binding was seen when ALS and control patient IgGs were tested against plastic-bound muscle cytoskeletal proteins, muscle cytosolic proteins, or GM, gangliosides in ELISA. Further no ALS IgG-specific interaction was noted to various purified proteins from muscle membranes, including Ca++ ATPase, calsequestrin, or the ryanodine receptor (all tested at 1–3 $\mu$g/ml plating concentration). Fractions enriched in the $\alpha_2\delta$ and $\beta$ subunits of rabbit skeletal muscle L-type calcium channel complex (each containing essentially no intact $\alpha_1$ subunit as determined with SDS-polyacrylamide gel electrophoresis) likewise demonstrated no differential binding of ALS and control IgG.

Observed responses of both sera and IgGs with calcium channel antigen in ELISA were slow in their development, requiring at least one hour incubation with pNPP substrate to become evident, and several hours incubation to become significant. While more rapid reactions were seen with higher concentrations of IgG (greater than 10 $\mu$g/assay) or serum (less diluted than 1:250) concentrations, specificity was simultaneously reduced. Greatest specificity for ALS IgG binding was noted with lower IgG concentrations (<5 $\mu$g/assay), or with greater serum dilutions (>1:1250).

Relationship of ELISA to disease progression

Figure 4A:
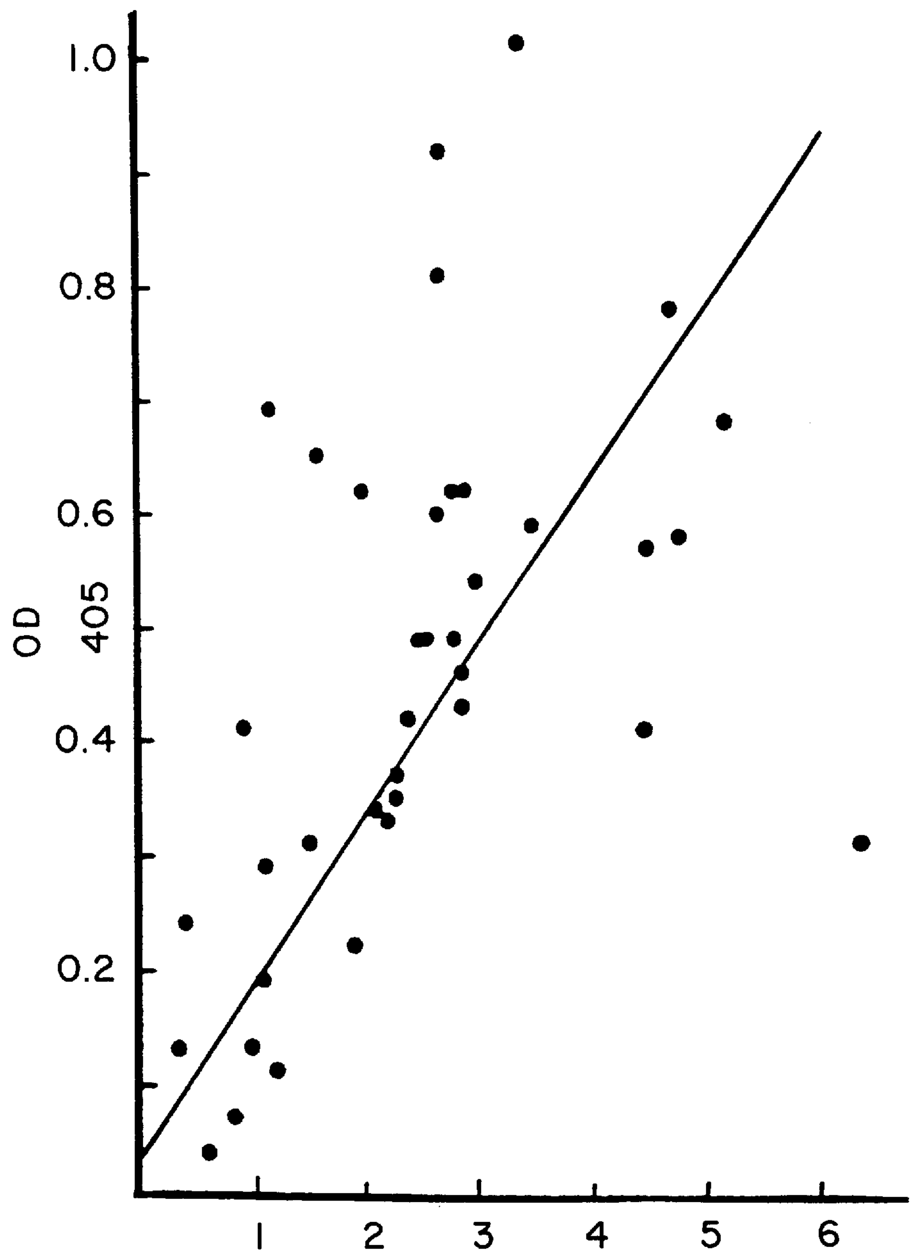
FIGS. 4A and 4B show the evolution of ALS patient serum ELISA reactions as a function of individual patient disease progression rates.
Figure 4B:
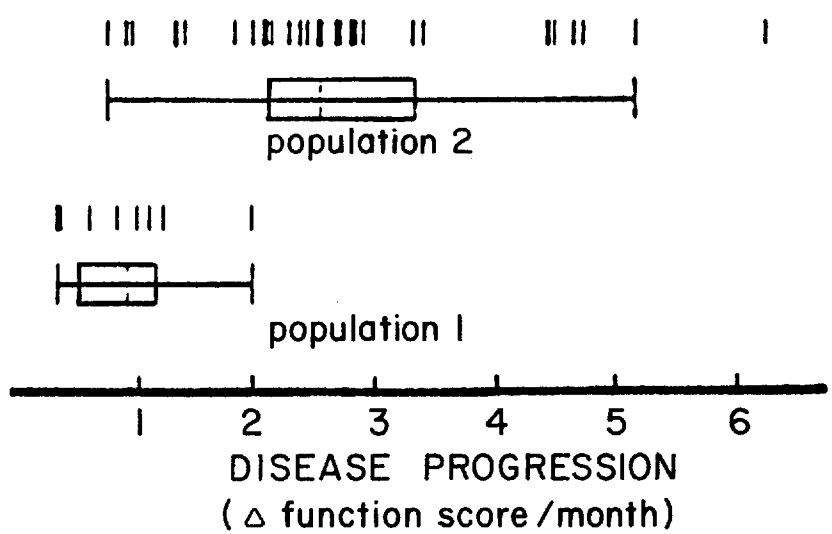

To determine whether the concentration of antibodies directed against calcium channel components in ALS patients related to their rates of disease progression, Baylor ALS disease scores were obtained for 38 of these individuals for a one year period surrounding the time of sample serum acquisition. Progression of disease was expressed as the change in function scores per month. When disease progression scores for each patient were rank ordered with their reaction in ELISA assay (FIG. 4A), moderately good direct correlation was found to exist (Spearman rank correlation= 0.618). When the ALS population was further differentiated into two groups based on their reaction in the ELISA assay (FIG. 4B), two disease progression groups were likewise defined (two sample Wilcoxan rank-sum z statistic=−4.17, $|z|<0.0001$). Strong correlations exist between the population that reacted poorly in this assay and that which had slow clinical disease progression, as well as with the population that was significantly reactive and that with more rapid progression of disease.

This relationship between serum ELISA reaction and ALS disease progression rate was not dependent upon the severity of patient disease at the time of assessment, nor on the age or sex of the affected patients in this population. Given the limitation that all tested patients were drawn from an outpatient clinic population, no apparent correlation was found between patient disease severity (according to the Baylor scale) and their ELISA reactivities. For the ALS population tested above, the Spearman rank correlation coefficient was 0.164, while for three patients tested longitudinally over 20 months with three serum evaluations, titer variation between samples was less than 20%. Patient age likewise did not correlate with disease progression rate or ELISA response (Spearman rank correlation coefficients of 0.012 and −0.187, respectively). Finally, the relationship between ELISA reaction and rate of disease progression was likewise not qualitatively affected by the sex of ALS patients, with good sex-specific Spearman correlation coefficients still found (0.734 for females, and 0.539 for males).

DISCUSSION

Using an ELISA technique, our results demonstrated the presence of calcium channel reactive immunoglobulins in ALS sera as well as in purified IgG fractions obtained from ALS patients. Further, IgG prepared from ALS patients used to document electrophysiologic interactions with voltage-gated calcium channels, also bound to purified calcium channel proteins in ELISA. Using this assay, the sensitivity of ALS IgG binding to solubilized L-type calcium channel increased with the purity of the plated antigen, presumably as a result of increasing the density of relevant binding sites applied to the plate. Greatest sensitivity was noted for highly purified antigen (applied at a density of approximately 20 fmol/microtiter well). IgG binding to antigen was not qualitatively affected by the method of channel purification. Selectivity of the ELISA interaction, both for ALS patients and for antigen, was also noted. When sera were tested, there was clearly more IgG binding to purified L-type calcium channel for the majority of ALS patients, than for age- and sex-matched normal and disease controls. While ALS sera that tested negatively were indistinguishable from controls and might represent a separate group of patients (i.e., spontaneous genetic mutation), better differentiation of ALS and control populations was observed when purified channel antigen or immunoglobulin were used. Almost no overlap was noted between ALS and control populations when testing using both purified antigen and IgG. Thus, as the sensitivity of the assay was increased, “false negative” rates were reduced, and the selectivity for ALS sera improved.

Likewise, only 4 of 75 non-ALS patients had strongly reactive (“false positive”) sera in our assay. Two sera were from patients that may have had atypical presentations of sporadic ALS, one of whom previously had been documented to have intramotoneuronal accumulations of IgG by immunohistochemical localization. The remaining strongly reactive sera (and immunoglobulins) were from two of three patients tested with Lambert-Eaton myasthenic syndrome (LEMS). LEMS is an autoimmune disease affecting motoneuron presynaptic N-type voltage-sensitive calcium channels. These channels have immunologic and pharmacologic similarities to L-type channels. Furthermore LEMS antibodies have been demonstrated to alter L-type calcium channels in bovine adrenal medullary cells. A possible explanation is that LEMS antibodies recognize epitopes on L-channels common to both calcium channel subtypes. In our studies, neither LEMS nor ALS antibodies bound to the structurally different ryanodine-sensitive calcium channel purified from skeletal muscle.

In electrophysiologic experiments on isolated skeletal muscle L-type calcium channels, ALS antibodies react only with the extracellular portion of the calcium channel, and not the intracellular portion. Alteration in charge movement and calcium current were observed when ALS IgGs were applied to skeletal muscle in vitro, or when these same ALS IgGs and their Fab fragments were added to L-type calcium channels from functionally reconstituted transverse tubules in a lipid bilayer system.

As stated above, the presence of voltage-dependent calcium channel antibodies is relatively specific for ALS. The only other known disorder with significant titers is LEMS, and in LEMS the pathophysiology of motoneuron damage is also related to calcium channel antibodies. In the case of LEMS, however, passive transfer of IgG from affected patients to mice results in a reduction of calcium channel flow and MEPP frequency, while with ALS IgGs, the opposite is seen. At LEMS neuromuscular junctions, antibodies produce both a reduction in the number of presynaptic voltage-gated calcium channels, and morphologic disorganization of the structure of such sites. In ALS muscle, though, the number of dihydropyridine sensitive channels is not reduced, and is increased in some cases. The different effects of calcium channel antibodies in LEMS and ALS may relate to different recognized epitopes mediating different consequences for motoneuron function in these diseases, akin to the opposite effects of autoantibodies to the thyrotropin (TSH) receptor observed in Graves disease and in Hashimoto's thyroiditis, depending upon the TSH receptor domain to which IgG is bound.

ALS sera contain antibodies against muscle L-type calcium channels, when the disease primarily affects motoneurons. This reaction of serum constituents or immunoglobulin fractions to peripheral L-type channels suggests binding of antibodies originally directed against similar but separate classes of neuronal voltage-dependent calcium channels. Also, in ELISA the long development times required for reaction suggest the presence of low concentrations of serum antibodies directed against an L-type calcium channel antigen, as a consequence of limited cross reaction by those antibodies actually produced to other epitopes, for example, central L- or N-type channels. As previously mentioned, the L-type calcium channel consists of multiple subunits that together comprise a voltage-gated calcium selective pore. Structural similarities, and immunologic cross-reactivity have already been demonstrated between several subunits of peripheral and central calcium channels. Without wishing to be bound by any theory, trauma and/or other insults may expose normally protected muscle and/or neuronal sites to the immune system and result in antibody production to a central voltage-sensitive calcium channel that cross-reacts more weakly with peripheral L-type channel proteins. Alternately, transient exposure to a toxin or infectious agent may result later in the production of cross-reactive antibodies.

Second Set of Experiments

METHODS

Western Blot

Voltage-dependent L-type calcium channels were purified as in Schneider et al. (described below). Highly purified calcium channel proteins first underwent gel electrophoresis through a 7.5% polyacrylamide matrix in the presence of 0.1% sds AND 5 mM dithiothreitol, and resulting gels were transferred onto polyvinylidine difluoride (PVDF) paper. After blocking for one hour at room temperature with phosphate buffered saline containing 1% BSA, 0.5% TWEEN-20 (PBS-BT), strips containing 0.2 ug protein were cut from this paper and incubated overnight with PBS-BT containing 100 $\mu$g/ml aliquots of IgG either obtained from 11 ALS patients, from 6 patients having known autoimmune disease with neurologic sequelae, or from 6 healthy individuals. Following a thorough wash to remove unbound human antibody, retained immunoglobulin was identified by horseradish peroxidase-coupled sheep-antihuman IgG, and visualized using the ECL enhanced chemiluminescence detection system (Amersham).

ELISA

The $Ca^{2+}$ channel ELISA used was a modification of the ELISA described above. Equal 100 μl aliquots of 20.0% (v/v) TWEEN-20, 1% 9w/v) BSA in phosphate buffered saline solution (PBS-BT:pH 7.4), containing 100 μg/ml IgG prepared from each of 13 ALS patients, 11 healthy age-matched individuals, and 14 patients with autoimmune neurologic disease, were separately pre-incubated in rows of blocked, $Ca^{2+}$ channel-containing microtiter wells (Corning 96-well ELISA plates) for 2 hours at 37° C. Following nine washes with a 0.9% NaCl/0.5% TWEEN 20 solution, duplicate wells in each treated row were incubated for an additional 2 hours at 37° C. with 100 μl of calcium channel subunit-specific mouse antibody, serially diluted to 508 different concentrations with PBS-BT. After extensive washing, 100 μl/microtiter well of alkaline phosphatase-conjugated goat anti-mouse antibody (without human IgG crossreactivity, 1:8000 dilution—Tago) was added at 37° C. for one hour. Plates were then washed an additional 9 times, and 0.4 mg/ml para-nitrophenyl phosphate in 1 mM $Mg_2CO_3$ (alkaline phosphate substrate: pH 9.4) for 3 hours at 37° C. Absorbance of colored product was measured at $OD_{405}$, after subtraction of $OD_{405}$ background absorbance, on a Bio-Tek wavelength EL311 microplate reader. Titer curves were assembled from mean absorbance values for each mouse antibody concentration, and slopes of logarithmic regression analysis ($r^2>0.9$) were then obtained from each curve. Human antibody (HAb) induced % inhibition of $Ca^{2+}$ channel:subunit-specific mouse antibody ($Ca^{2+}$ CssMab) complex formation was calculated by the equation: 1-(slope HAb pre-incubated $Ca^{2+}$CssMAb titer curve/slope Ca 2+CssMAb titer curve).

DISCUSSION

Figure 5:
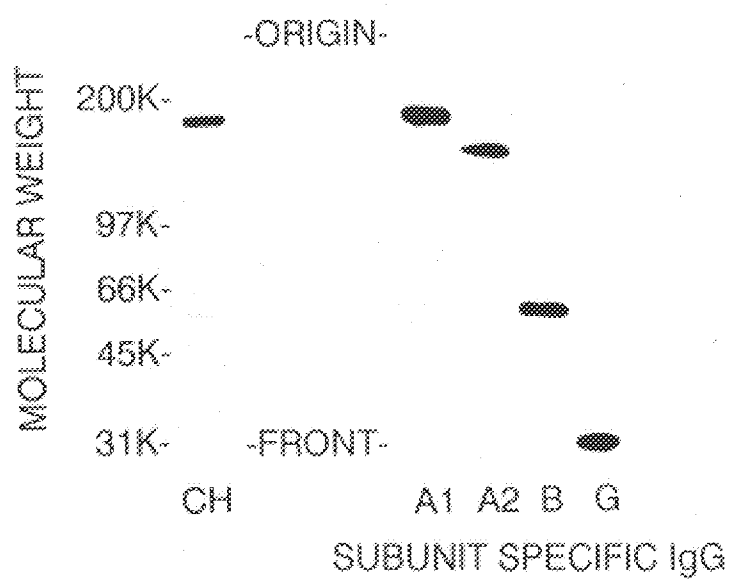
FIG. 5 depicts the reaction of purified calcium channel subunits (silver-stained lane on left) with subunit directed Abs from $\alpha_1$, $\alpha_2$, β, and gamma subunits, as shown on immunoblot on right. Poor reactivity of the $\alpha_2$ subunit by silver stain is the result of its large sugar residue content.
Figure 6A:
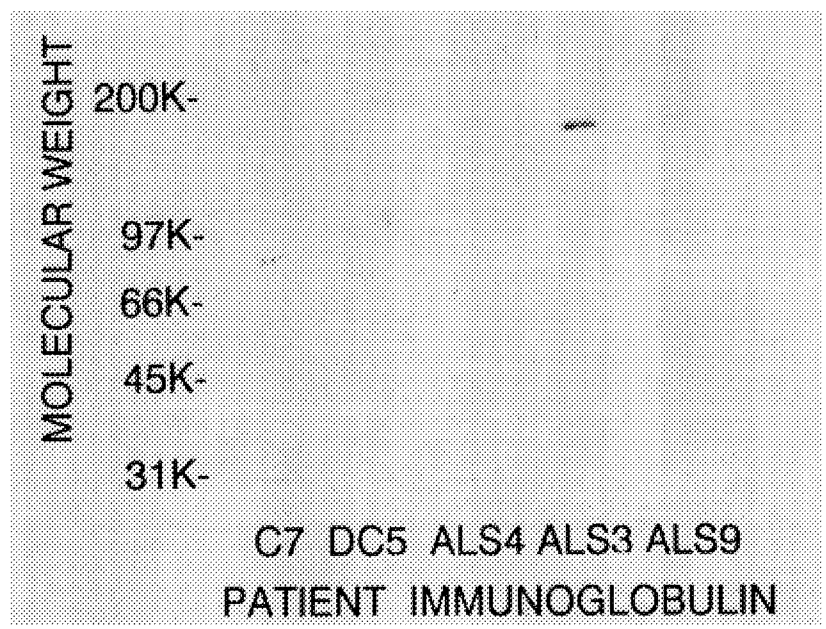
FIG. 6A shows the direct binding of ALS IgG to the $\alpha_1$ subunit, as observed on immunoblots of $Ca^{2+}$ channel tested with immunoglobulins from three ALS patients: ALS4, ALS3 and ALS9. Weak binding is shown with ALS9 IgG. No binding was found for the two depicted controls: C7 and DC5. All human immunoglobulins were incubated for 6 hours at 25° C., using equal 100 $\mu$g/ml IgG concentrations. Patient numbers correspond to those seen in all other figures and in table 1.

Western transfer immunoblots document specific interactions between L-type voltage-dependent calcium channels and immunoglobulin isolated from the sera of ALS patients. On silver-stained gels, profiles of purified calcium channel proteins revealed separate $alpha_1$ (170 Kd), $alpha_2$ (145 Kd), beta (53 Kd), gamma 32 Kd), and delta (28 Kd) subunits, as identified by subunit-specific antibodies (FIG. 5). Immunoglobulins purified from 7 of the 11 tested ALS patients labeled an immunoblot protein band migrating identically with the 170 Kd calcium channel $alpha_1$ subunit (FIG. 6A). This band was likewise recognized by $alpha_1$ subunit-specific monoclonal antibodies. No other channel subunit was bound by ALS IgGs on immunoblot, nor did IgGs obtained from age and sex-matched normal individuals and patients with autoimmune disease react with any of the transferred calcium channel subunits.

Figure 6B:
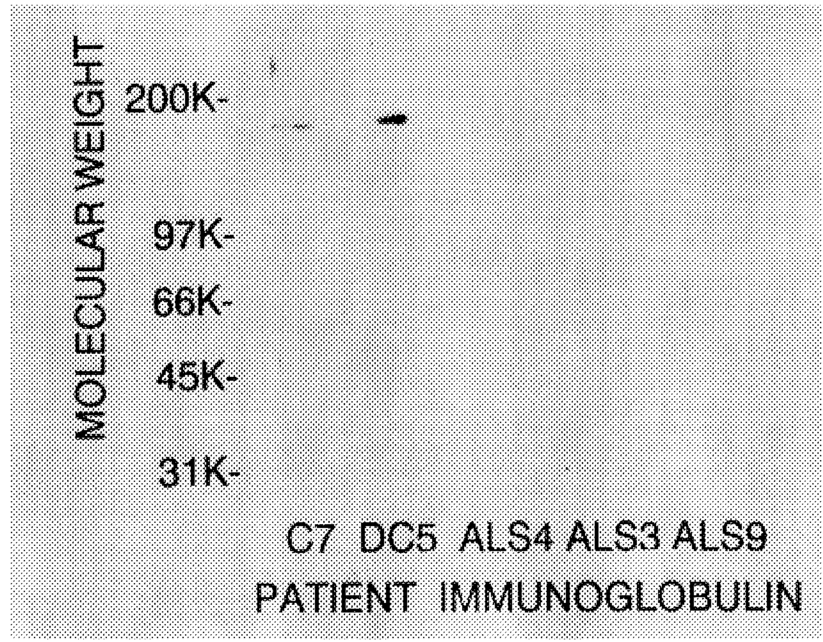
FIG. 6B shows the same immunoblot as observed in FIG. 6A, after subsequent addition of 8B7 mAb. Complete blockade of binding is found for two ALS IgG-treated lanes with partial blockage of the mAb by ALS9 IgG. Good binding by the 8B7 mAb to the $\alpha_1$ subunit is seen in the two control patient IgG-pretreated lanes.

ALS patient IgGs also block the specific interaction of an $alpha_1$ subunit-specific mouse monoclonal antibody (8B7 mAb) with its calcium channel ligand. 8B7 mAb was prepared by immunizing mice with purified calcium channel, producing hybridomas therefrom and screening those hybridomas by immunoblot for reactivity with the $\alpha_1$ subunit. Binding of this antibody was prevented when blocked polyvinylidine difluoride (PVDF) immunoblot strips containing electrophoresed calcium channel proteins were preincubated for one hour with IgG (100 μg/ml) derived from ALS patients, prior to the addition of just-saturating concentrations of the 8B7 mAb (ng/ml; FIG. 6B). The apparent degree of inhibition of monoclonal antibody-$alpha_1$ subunit complex formation was directly dependent on the concentration of ALS IgG used in the initial incubation step, and upon the patient from whom the IgG was derived. IgG prepared from healthy individuals and from patients with autoimmune disease had no effect on the attachment of the 8B7 mAb to the immobilized $alpha_1$ subunit, even when tested at high (1 mg/ml) concentrations. Interestingly, for most of the tested patient immunoglobulins, ALS IgG-induced blockade of $alpha_1$ mAb binding on immunoblot appeared to provide a more sensitive assay for IgG-$Ca^{2+}$ channel $alpha_1$ subunit interactions than did direct binding by ALS immunoglobulins. However, one patient with ALS apparently had calcium channel antibodies that were detected by direct immunoblot of the $alpha_1$ subunit, but that were not effective in blocking 8B7 mAb binding. We believe that the direct assay is preferable in that it presently appears to reduce the number of false negatives.

Figure 7:
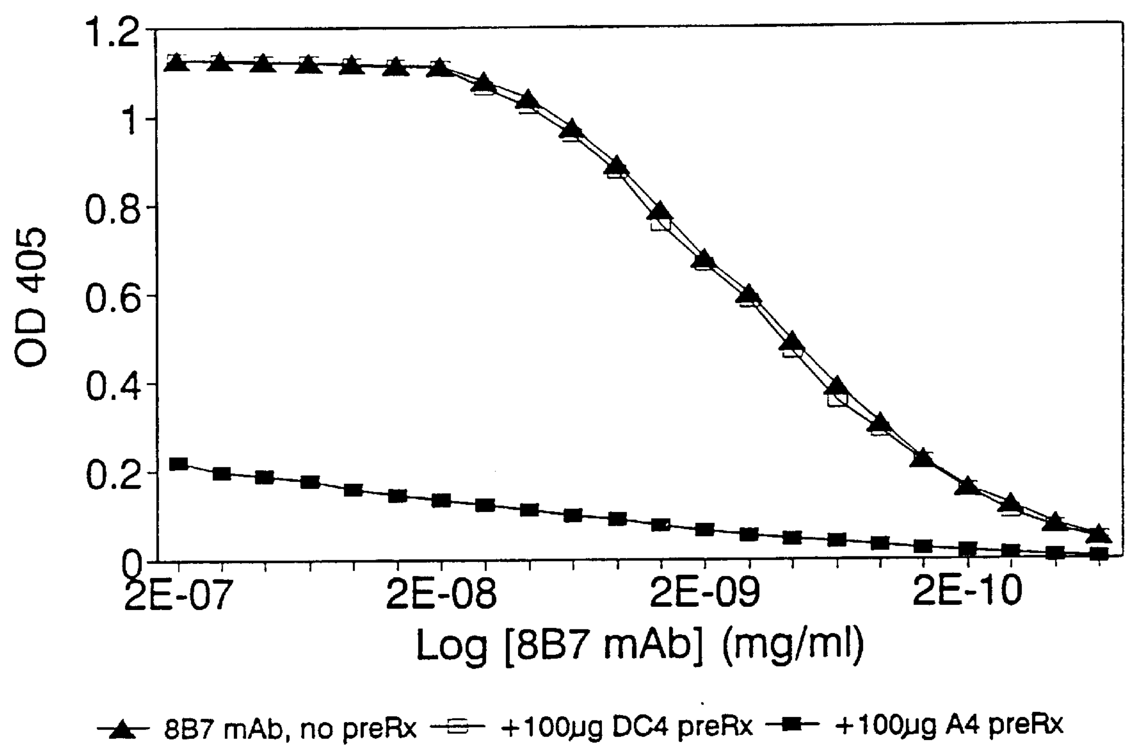
FIG. 7 depicts the results of an experiment showing the blockage of 8B7 mAb binding by preincubation with ALS4 IgG ("A4 pre Rx"), without significant blockage by preincubation with DC4, i.e. control, IgG ("DC4 pre Rx").
Figure 8A:
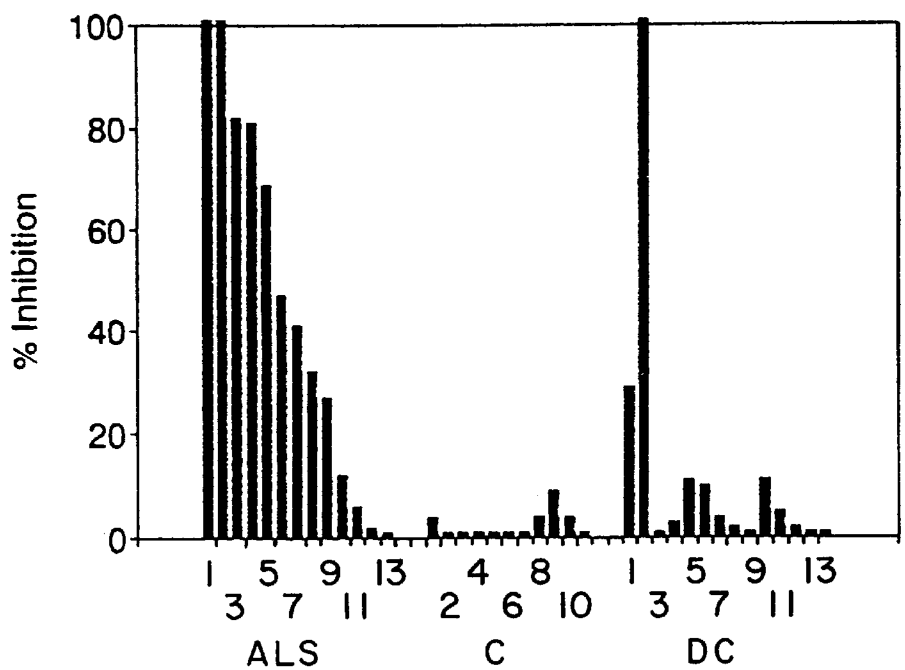
FIGS. 8A–8C shows binding inhibition data for IgG from 13 ALS patients, 11 normal individuals (C), and 14 patients with autoimmune neurologic disease (DC).
Figure 8B:
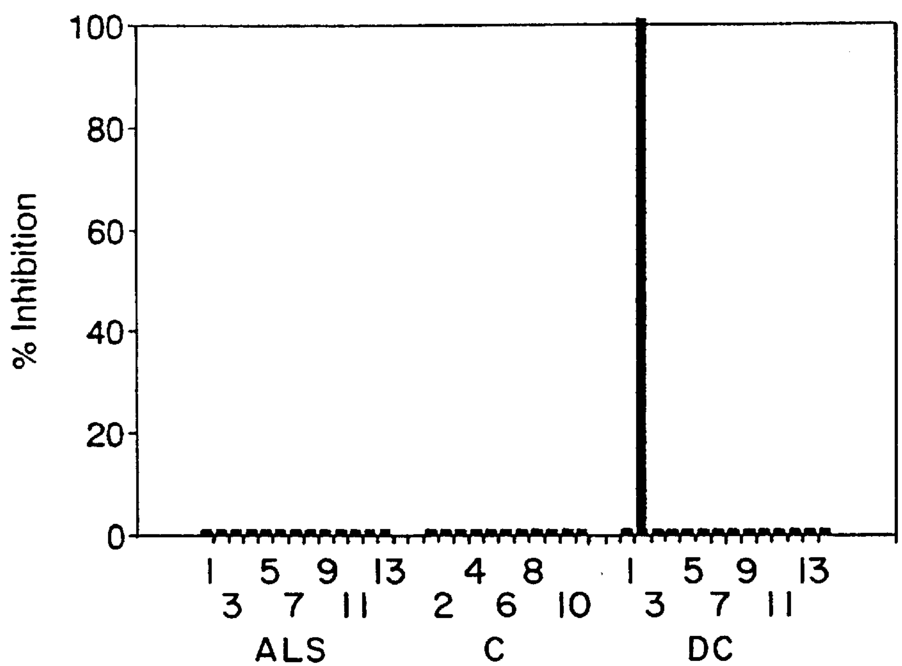
Figure 8C:
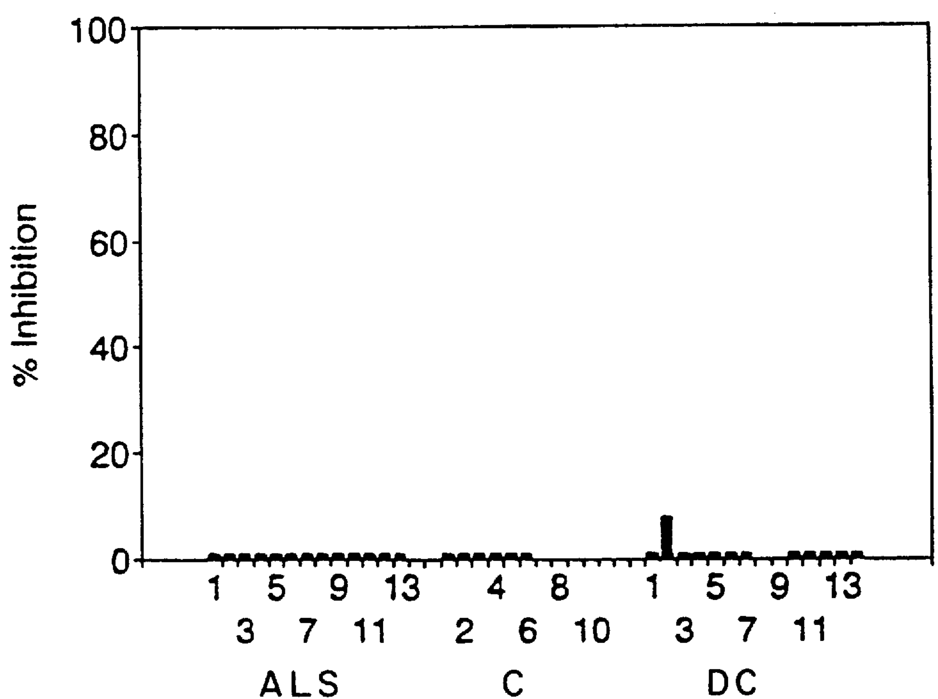

ALS IgG-induced blockade of 8B7 mAb-$Ca^{2+}$ channel association was also detected by ELISA. As depicted in FIGS. 7 and 8A, when 8B7 mAb binding curves were tested with or without human IgG preincubation, IgGs (tested at 100 μg/ml concentration) purified from 9 of 13 tested ALS patients inhibited by greater than 25% the association of 8B7 mAb and $Ca^{2+}$ channel protein. IgG obtained from the sera of 12 age and sex-matched normal individuals and from 12 of 14 age and sex-matched diseased patients, when tested at equal 100 μg/ml concentrations, produced less than a 10% decrease in 8B7 mAb binding (FIG. 8B, 8C). However, immunoglobulins from two non-ALS patients significantly inhibited 8B7 mAb-Ca2+channel binding. Both of these patients—one with Lambert-Eaton myasthenic syndrome and one with Isaac's syndrome—have diseases previously described as autoimmune, antibody-mediated ion-channel disorders. Immunoglobulins from patients with Lambert-Eaton syndrome are known to interact with the voltage-dependent calcium channel, and while the antigenic target in Isaac's syndrome has not been defined, plasmapheresis has sometimes provided significant clinical benefit for affected individuals.

In contrast, preincubation of purified L-type voltage-gated $Ca^{2+}$ channel subunits with ALS IgG did not block the binding of an anti-beta subunit-specific monoclonal antibody 7C3 to immobilized calcium channel antigen on immunoblot, or in ELISA (FIG. 8B). This apparent lack of ALS patient antibody binding directed against the cytoplasmic beta subunit, both as assessed by direct immunoblot, and as determined by monoclonal antibody inhibition studies, might be expected if such antibodies required access to external binding epitopes to produce disease.

Potential evidence for this hypothesis is that neither ALS nor control IgGs block the binding of an $alpha_1$ N-terminal cytoplasmic sequence site-specific antibody to its intracellular ligand, as assessed by ELISA (FIG. 8C). For these experiments, the addition of 0.01% triton X-100 to the plated calcium channel antigen was necessary in order to expose the N-terminal sequence mAb binding site. After triton addition, the binding of the 7C3 beta subunit mAb to Ca channel increased three-fold, suggesting disruption of previously documented polarization of $Ca^{2+}$ channel complex in digitonin micelles; the addition of .01% triton X-100 likewise decreased the binding of the 8B7 mAb to the $alpha_1$ subunit almost 4-fold, but did not alter the blockade by most ALS antibodies.

As also shown in direct immunoblot assay, however, the ELISA suggests specificity of the ALS antibodies for the $alpha_1$ subunit, rather than for all external membrane-facing subunits. ALS immunoglobulins had no blocking effect on the reaction of $alpha_1$ or gamma subunit-specific polyclonal antibodies with their respective ligands.

Interestingly, IgG obtained from the LEMS patient, when tested in ELISA or on immunoblot at 100 μg/ml concentration, could be differentiated from all ALS patient IgGs, normal individual IgGs, and IgGs from patients with other autoimmune neurologic diseases by its unique ability to also prevent the binding of anti-beta 7C3 mAb to the beta subunit (FIG. 8B). This blockade was unchanged after triton X-100 addition, and has been subsequently observed with partially purified immuno-globulins obtained from three of four additional tested LEMS patients (all of which had been first shown to be reactive against the alpha$_1$ subunit).

When results from the direct actions of ALS immunoglobulin on calcium channel protein immunoblots were combined with those obtained by the blockage of 8B7 mAb-$Ca^{2+}$ alpha$_1$ subunit association on immunoblot and on ELISA, 75% of ALS IgGs yielded positive results in one or both assays (Table shown in FIG. 9). These data are similar to our results above using an ELISA to document the direct binding of ALS antibodies to L-type voltage-dependent calcium channels, where 80% of 48 ALS patient sera had significantly higher reactivity in ELISA than observed for 75 sera from patients with other non-autoimmune motoneuron diseases, patients with other non-autoimmune and autoimmune neurologic diseases, or with healthy volunteers. When both purified immunoglobulins and L-channel complexes were used in direct ELISA, there was little overlap between the ALS and control populations. As noted above, one of the two ALS IgGs that did not react in this study on immunoblot or by blocking ELISA, has been observed to react weakly with $Ca^{2+}$ channel antigen in direct ELISA. As also observed here, LEMS patients' sera and IgGs provided the other group of significant reactors with immobilized $Ca^{2+}$ channel in ELISA.

The 8B7 mAb-blocking ELISA provides similar specificity to that observed in direct binding ELISA. However, it has inherently decreased overall sensitivity, resulting from the lack of mAb-blocking antibodies in some ALS patient IgGs, an important disadavantage which makes the direct assay more useful at present. Nevertheless, the mAb blocking (i.e. competitive) assay has the advantage of being much more sensitive (and hence, more rapid) with respect to antigen labeling. It relies on the reaction of known concentrations of a high affinity alpha$_1$ -specific monoclonal antibody with its ligand, rather than on the direct binding of polyclonal ALS antibodies to the $Ca^{2+}$ channel. Practically, it also appears to be less altered by methods of antigen preparation, or by the effects of partial channel subunit proteolysis or conformation change that may variably occur during $Ca^{2+}$ channel preparation or with storage.

Differences in the reactivities of ALS patient IgGs between direct immunoblot and mAb indirect blocking assays may be due in part to the observation that most patients with autoimmune disease make antibodies to multiple epitopes of disease-relevant antigens, and the repertoire of such antibodies may vary considerably among patients. This variability may explain why immunoglobulins from one ALS patient bound immobilized $Ca^{2+}$ channel on direct immunoblot, and yet not block the binding of a mAb potentially reacting with a different epitope on the same subunit. Reaction of ALS antibodies in direct ELISA but not by direct immunoblot (seen with 4 patient IgGs) may instead be explained either by the reaction of antibodies with conformation-dependent epitopes that are altered or lost with denaturation, or by the greater sensitivity of the ELISA relative to most immunoblot reactions.

The noted blockage of 8B7 mAb-$Ca^{2+}$ binding in ELISA suggests either that ALS IgGs directly compete with the mAb for specific epitope, or that ALS IgGs act allosterically to prevent mAb binding through changing the alpha$_1$ subunit conformation. For most ALS patient IgGs, the latter explanation seems less likely, based on similar inhibition results obtained using immunoblot of denatured SDS-treated calcium channel antigens.

ALS patient antibodies may also selectively bind to the external surface of the alpha$_1$ subunit, since such antibodies do not block the binding of either the cytoplasmic domain alpha$_1$ mAb or the beta mAb to their respective epitopes, but do block the binding of an alpha$_1$ subunit-specific mAb produced against native conformation L-type calcium channel (8B7 mAb). Direct interaction of 8B7 mAb with preplated $Ca^{2+}$ channel micelles in ELISA is reduced under conditions which alter the orientation of the alpha$_1$ subunit in the membrane, at the same time that cytoplasmic epitopes become more accessible to their antibodies.

Purification of L-type calcium channels (Schneider et al. method)

MATERIALS FOR PURIFICATION

General points

All buffers contain aliquots of the following protease inhibitor stock solutions:

a) 300 mM iodoacetamide in water b) 1M 1.10-phenanthrolin in 100% ethanol c) 100 mM PMSF in 100% ethanol (to be added last)

d) 1 mg/mL antipain in 50% ethanol e) 1 mg/mL leupeptin in 50% ethanol f) 1 mM pepstatin a in 50% ethanol g) 1 M benzamidine in 50% ethanol h) aprotinin 1 mg/ml in water The stock solutions are kept at −20° C. and aliquots are added to all buffers immediately before use. The stock solution a) and b) through g) are diluted 1:300 and 1:1000 fold, respectively.

Digitonin is prepared as a 3% stock solution in water. Batches of digitonin are different in quality and are tested for purity and solubility. The solubility is checked with a 3% solution after stirring the suspension for 24 hours at 4° C. Only batches with a solubility of 90% or better should be used. All buffers which contain digitonin are filtered through cellulose acetate filter (pore size 0.45 $\mu$m).

Buffers

Buffer A (preparation of microsomes):

20 mM Mops/KOH, pH 7.4 (at 4° C.)

10 mM EDTA 300 mM sucrose

Buffer B (labeling and solubilisation of the CaCB-receptor (receptor for calcium channel blockers)):

10.0 mM Hepes/KOH, pH 7.4 (at 4° C.)

185.0 mM KCL 1.5 mM $CaCl_2$

Buffer C (WGA-lectin chromatography, regeneration):

0.1 M Tris/HCl, pH 8.5

0.5 M NaCl 0.05% (m/v) $NaN_3$

Buffer D (WGA-lectin chromatography, regeneration):

0.1 M sodium acetate, pH 5.0

0.5 M NaCl

Buffer E (WGA-lectin chromatography):

10.0 mM Hepes/KOH, pH 7.4 (4° C.)

100.0 mm KCl 1.5 mM $CaCl_2$ 0.2% digitonin

Buffer F (WGA-lectin chromatography):

10.0 mM Hepes/NaOH, pH 7.4

40.0 mM NaCl 1.5 mM $CaCl_2$ 0.1% digitonin

Buffer G (DEAE-Ion exchange chromatography):

10.0 mM Hepes/NaOH, pH 7.2 (at 4° C.)

50.0 mM NaCl 1.5 mM $CaCl_2$ 0.1% digitonin

Buffer H: as buffer G except containing 250 mM NaCl (final concentration).

Buffer I (sucrose density gradient, DHP-binding):

10.0 mM Hepes/NaOH, pH 7.4 (at 4° C.)

1.5 mM $CaCl_2$ 0.1% digitonin

Buffer K (sucrose density gradient, phenylalkylamine binding):

10.0 mM Hepes/NaOH, pH 8.0 (at 4° C.)

0.1% digitonin

Columns:

WGA-lectin chromatography

Precolumn: 10 mL (settled volume) Sepharose 4B

Column: 30 mL wheat germ agglutinin (WGA) sepharose 6 MB

DEAE-Ion exchange chromatography

Precolumn: TSK DEAE-5PW, 6×10 mm

Column TSK DEAE-5PW, 21.5×150 mm

BUFFERS AND SOLUTIONS USED FOR THE IDENTIFICATION

Reversible binding of dihydropyridines

Buffer L: 2.0 mM Mops, pH 7.4 (at 4° C.)

0.6 mM $CaCl_2$

8% sucrose 0.5% digitonin

Buffer M: 100 mM Hepes/NaOH, pH 7.4 (at 4° C.)

1.2 mM $CaCl_2$

16% sucrose 0.05% digitonin

Solution N: 50 nM [$^3$H](+)isradipine in 5% ethanol (70–80 cpm/fmol) (PN200-100; NEN Chemical)

Buffer P: 100 mM Hepes/NaOH, pH 7.4, 30% (m/v) polyethyleneglycol (PEG) 6000

Solution Q: 5 mg/mL IgG, 5 mg/mL bovine serum albumin

Buffer R: 100 mM Hepes /NaOH pH 7.4, 8.5% PEG 6000

Reversible binding of phenylalyklamines

Buffer S: 30.0 mM Hepes/NaOH, pH 8.0 (at 4° C.)

0.075% digitonin 5.0 mM CaEGTA 5.0 mM EGTA

Buffer T: 20.0 mM Hepes/NaOH, pH 7.2 (at 4° C.)

0.05% digitonin

Solution U: 240 nM [$^3$H](−)desmethoxyverapamil (20–23 cpm/fmol) in 5% ethanol

Buffer V: 22.5 mM acetate/NaOH, pH 5.3

280.0 mM sucrose 5.63 MM EDTA 11.25% polyethyleneglycol 6000

Irreversible binding of dihydropyridines

UV-light: 200 W lamp (260–320 nM)

Buffer W: 20.0 mM Hepes/NaOH, pH 7.4 (at 4° C.)

1.5 mM $CaCl_2$

5% sucrose 0.05% digitonin

Buffer X: 10.0 mM Hepes/NaOH, pH 7.4 (at 4° C.)

0.05% digitonin

Radioligand: 400 nM [$^3$H]azidopine in 10% ethanol (48 cpm/fmol)

Unlabeled ligand: 200 μM (±)isradipine (PN200-110)

Irreversible binding of phenylalkylamines

Radioligand: 200 nM [$^3$H]Lu 49888 in 5% ethanol

200 μM (±)devapamil

METHHODS

PURIFICATION OF SKELETAL MUSCLE CaCB-RECEPTOR

Purification scheme

The following scheme outlines the purification steps which low the purification of 3.0 mg pure CaCB-receptor.

| | | Protein (mg) |
|---|---|---|
| | The back and leg muscle of 2 rabbits | 700,000 |
| 1 | ↓ | |
| | Crude microsomes | 500 |
| 2 | ↓ | |
| | Solubilized CaCB-receptor | 220 |
| 3 | ↓ | |
| | WGA-column eluate | 4 |
| | (6 × WGA eluates) | 24 |
| 4 | ↓ | |
| | DEAE-ion exchange column eluate | 8 |
| 5 | ↓ | |
| | sucrose gradients | 3 |

Purification method

Prepration of microsomes

Microsomal membranes are prepared from white rabbit skeletal muscle.

1. Two rabbits are sacrificed and bled. The back and leg muscles are immediately excised and kept on ice. All further steps are carried out at 4° C.

2. The connective tissue is removed and the muscle minced with scissors. The minced muscle (700 g muscle) is homogenized in a Waring blender for 30 sec at low speed and 30 sec at high speed (3 times) with 2100 mL buffer A. The homogenate is centrifugated (8600 x g, 10 min, 4° C.). The supernatant is filtered 4 times through cheese cloth.

3. The pellet is rehomogenized in a Waring blender for 15 sec at low and 15 sec at high speed with 1050 mL buffer A. The homogenate is centrifugated as in 2.

4. The supernatants (1700 mL) are combined and solid KCl is added to a final concentration of 0.6. M. The solution is stirred until the KCl is completely dissolved. The solution is then centrifugated (125,000 x g, 60 min, 4° C.).

5. The microsomal pellet is suspended in 800 mL buffer A with a glass/teflon homogenizer by two to three up and down strokes. The microsomes are resedimented (25000 x g, 40 min, 4° C.). The pellet is resuspended in 50 mL buffer A (final protein concentration between 15 and 20 mg/mL) and stored in 10 mL aliquots at −70° C.

This procedure yields 70–100 mg microsomal protein per 100 g wet weight muscle containing 10.5±1.9 pmol (n=13) isradipine binding sites/mg protein determined as in Catterall et al. (1988).

Labeling and solubilisation of the CaCB-receptor

About 5% of the binding sites of the CaCB-receptor are labeled by the dihydropyridine [$^3$H](+)isradipine ((+) PN200-110; NEN Chemicals) to follow the CaCB-receptor during the purification.

1. Radioactive labeling is carried out immediately before solubilization of the CaCB-receptor. The microsomal membranes of step 1 (500 mg) are thawed and diluted with cold buffer B containing 1 mM EDTA to a volume of 200 mL.

2. 200 mL of 1 μM [$^3$H](+)isradipine in 10% ethanol is added (final concentration 1 nM). The suspension is mixed and incubated for 90 min at 4° C.

3. The suspension is centrifugated (114,000 xg, 30 min, 4° C.).

4. The resulting pellet is resuspended in 30 mL of buffer B containing 1% digitonin and disrupted in a glass/teflon homogenizer by 6 up and down strokes.

5. The suspension is diluted further with buffer B containing 1% digitonin to a final volume of 200 mL.

6. After 40 min, the suspension is centrifugated (114,000 x g, 30 min, 4° C.). The supernatant is retained.

7. The protein concentration and amount of bound isradipine is determined in aliquots.

WGA-lectin chromatography

Column handling: 1. The pre-column material is renewed for each run. The pre-column and column are connected and are equilibrated overnight with 200 mL buffer B containing 0.3% digitonin.

2. The WGA-column can be used at least 15 to 17 times. This is equal with the solubilization of 10 g microsomes during 15 to 17 runs. The column can be used thereafter if the amount of solubilized protein loaded onto the column is decreased.

3. After each run the WGA-column is washed at room temperature with 50 mL buffer C containing 1% digitonin. The buffer is circulated overnight through the column. Thereafter, 200 mL each of buffer C, D and B are passed over the column at 4° C.

Column chromatography: 1. The supernatant from 2: is passed through a cellulose acetate filter (pore size 0.45 μm) and diluted 1.5-fold with buffer B containing 0.1% digitonin.

2. The solution is then pumped through the tandem column system at a flow rate of 3 mL/min.

3. The columns are washed with 150 mL buffer E. The pre-column is disconnected.

4. The WGA-column is washed further with 50 mL buffer F.

5. The CaCB-receptor is eluted with 100 mL buffer F containing 0.3 M N-acetyl-D-glucosamine. Fractions of 4 mL are collected and their radioactivity and protein concentation is determined.

6. Peak fractions are pooled and stored at −70° C. in 10 mL aliquots. Five hundred mg microsomal protein yields 4.4 mg±0.9 (n=8) mg partially purified CaCB-receptor.

DEAE-Ion exchange chromatography

Column handling: 1. The columns are stored in water containing 0.05% sodium azide. Before use, 60 mL buffer G are pumped over the column at a flow rate of 2 mL/min.

2. At the end of each run, 60 mL buffer G containing 1 M NaCl (final concentration), followed by 500 mL water containing 0.05% sodium azide are passed through the columns. The content of the pre-column is renewed when the pressure increases.

3. The columns are extensively regenerated after 7 runs as recommended by the manufacturers. 500 mL of the following buffers are used at a flow rate of 2 mL/min. They are applied in a gradient with a steepness of 1%/min. Each gradient was separated by a wash with 500 mL water. The gradients are in the following order: 0.1 to 1 M NaCl, water, 0–20% methanol, water, 0 to 6 M guanidine/HCl, water 0 to 0.1 M acetic acid and water.

Column chromatography. The DEAE-5PW column chromatography is carried out with a two pump HPLC system.

1. The eluate of six WGA-columns (24 mg protein in 200 mL) are thawed and pumped through the HPLC-DEAE columns at a flow rate of 2 mL/min.

2. The columns are washed and eluted by a salt gradient generated by the pump controller according to the following scheme:

| Time (min): | 0 | 6 | 12 | 60 | 72 | 92 | 100 | 110 | 120 | |
|---|---|---|---|---|---|---|---|---|---|---|
| % buffer G | 100 | 100 | 62 | 56 | 56 | 28 | 28 | 0 | 100 | pump A |
| % buffer H | 0 | 0 | 38 | 44 | 44 | 72 | 72 | 100 | 0 | pump B |
| step | | | <---------wash---------> <elution>----wash----> | | | | | | | |

Fractions of 3 mL (every 1.5 min) are collected. The CaCB-receptor elutes at 78 min and at a NaCl concentration of 175 mM.

3. The radioactive peak fractions, which contain 8.0±1.3 (n=5) mg protein, are pooled and concentrated 30–100 fold by ultrafiltration using a Centricon-30 micro concentrator.

4. The concentrated sample is diluted tenfold with buffer I (see 5) and concentrated again in order to lower the NaCl concentration below 20 mM.

5. The concentrated sample (0.3–1 mL) is either stored at −70° C. or layered immediately on the top of 1 to 4 sucrose gradients.

Sucrose density gradient

Two or four 5–20% continuous sucrose gradients are prepared by mixing 2×19.8 mL of Buffer I containing 20% and 5% Sucrose. The gradient is pumped through a needle into 40 mL centrifugation tubes which must be sealed tightly as recommended by the manufacturers. The concentrated and desalted CaCB-receptor from step 4 (about 8 mg) is thawed and 0.3 - 0.5 mL aliquots containing maximally 2.5 mg protein are layered onto individual sucrose gradients. The tubes are sealed by melting and centrifugated in a vertical rotor (242,000 x g, 90 min, 4° C.). The gradient is pumped off from the bottom through a needle and fractionated into 2 ml aliquots. The peak fractions of protein bound radioactivity (peak at fraction 10; tube bottom is fraction 1) are determined. The peak fractions (fraction 8–11) are pooled and stored at −70° C. These fractions contain 3 mg purified CaCB-receptor.

The purified CaCB-receptor can be used directly for dihydropyridine binding studies. However, this preparation is not optimal for the study of the phenylalkylamine binding site, since the high calcium concentration inhibits binding to this site. For the latter purpose, the sucrose gradient buffer I is replaced by buffer K which does not contain added calcium.

IDENTIFICATION OF THE CaCB BINDING SITES

Reversible binding

The dihydropyridine binding site

1. The purified CaCB-receptor is diluted 50 fold with buffer L to a digitonin concentration of 0.05% and a protein concentration of 1 to 10 μg/mL. The solubilized receptor and the WGA-column eluate are diluted 20-fold.

2. For a binding experiment the following solutions are mixed in a plastic (polycarbonate or polypropylene)) tube:

75 μL buffer M

30 μL solution N, containing variable concentrations (5–50 nM) of the radioligand 15 μL 10% ethanol orr 15 μL 50 μM (±)isradipine in ethanol 30 μL CaCB-receptor diluted in buffer L 3. The binding is started by the addition of the receptor. Nonspecific binding by $^3$H (+) isradipine is determined in the presence of 5 μM (excess) unlabeled (±) isradipine in alternate tubes.

4. The incubation is terminated after 2 h at 4° C. or 1 h at 20° C. by adding 3×40 μL of the binding assay mixture to 200 μL ice-cold buffer P followed by the addition of 60 μL solution Q. The mixture is kept for 10 min on ice and is diluted further with 3.5 mL ice-cold buffer R.

5. The precipitated receptor-ligand-complex is collected on a Whatman GF/C filter. The filter is washed twice with 3.5 mL ice-cold buffer R.

6. The filter is placed into minivials (5 ml) and a toluene/triton-X-100 based scintillation cocktail is added. The retained radioactivity is determined in a scintillation counter.

The phenylalkylamine binding site

1. The purified CaCB-receptor is diluted to a digitonin concentration of 0.05% and a protein concentration of 2 μg/mL with cold buffer T.

2. For a binding experiment the following solutions are mixed in a plastic tube:

120 μL buffer S

30 μL solution U containing variable concentrations (8–240 nM) of the radioligand 30 μL 5% ethanol or 30 μL 500 μM desmethoxverapamil in 5% ethanol 60 AL CaCB-receptor diluted in buffer T 3. The binding is started by the addition of the receptor. Nonspecific binding is determined in the presence of 20 to 70 μM unlabeled desmethoxyverapamil in alternate tubes.

4. The incubation is terminated after 2 h at 4° C. by adding 2 mL ice-cold buffer V followed by the addition of 50 μL buffer Q. The mixture is kept for 10 min on ice.

5. The precipitated receptor-ligand-complex is collected on a Whatman GF/C filter. The filter is washed twice with 4 mL ice-cold buffer V.

6. The filters are transferred to minivials, to which 4.5 of a triton-X-100/toluene based scintillation cocktail is added. The radioactivity is determined in a scintillation counter.

IDENTIFICATION OF THE CaCB BINDING SITES BY IRREVERSIBLE BINDING

The dihydropyridine binding site

1. The purified CaCB-receptor is diluted with cold buffer X to a protein concentration of 80 μg/mL.

2. The receptor is incubated with the azido analog of dihydropyridine in the dark at 4° C. A red light is employed while handling azido-compounds.

3. The following buffers are mixed together in a well of titertek plate:

70 μL buffer W

35 μL radioligand (azidopine)

35 μL CaCB-receptor diluted in buffer X

4. The binding is started by the addition of 35 μL CaCB-receptor (80 μg/mL). Nonspecific incorporation is determined in the presence of 20 μM (±)isradipine.

5. After 90 min the plate is placed on ice under the UV-lamp for 5 minutes. The plate is rotated during photolysis.

6. The photolysed samples are denatured for 15 min at 37° C. in the presence of a 1.2% SDS and in the absence or presence of 250 mM 2-mercaptoethanol.

7. The peptides are separated on a 7.5% sodium dodecylsulfate polyacrylamide gel which is crosslinked by 0.3% diallyltartrardiamide. The incorporated radioligand is determined either by autoradiography of a stained gel or by cutting its lanes into 2 mm slices. Individual slices are cleaved by oxidation with 0.2 mL 2% sodium metaperiodate in 4% acetic acid at pH 3 for 3h at room temperature.

8. Thereafter, 4.5 mL of a triton-X-100/toluene based scintillation cocktail are added and the radioactivity is determined in a scintillation counter.

The phenylalkylamine binding site

The following buffers are mixed together in a well of a titertek plate:

70 μL buffer S

35 μL radioligand (the azido analog Lu 49888)

35 μL CaCB-receptor diluted in buffer X

Binding and photoincorporation is carried out as described for the dihydropyridine site using the azido analog of devapamil and buffer S. Nonspecific incorpoation is determined in the presence of 20 μM (±)devapamil.

NOTES

Purification

The major contaminating proteins have kDa's of over 300,110 and 60 and are removed during the WGA-lectin chromatography. The purified receptor contains five peptides. The $\alpha_1$-subunit (apparent kDa 165) contains the high affinity binding sites for dihydropyridines (isradipine), phenylalkylamines (devapamil) and benzothiazepines (diltiazem) and is thought to constitute, together with the β- and the τ-subunit, the ion channel. The $\alpha_1$- , β-, and τ-subunit are present in a 1:1:1 stoichiometry, whereas the stoichiometry of the $a_2$/δ-subunit is unclear at present.

IDENTIFICATION

The optimal binding of a dihydropyridine requires 0.1 to 1.0 mM free calcium whereas phenylalkylamine binding occurs only in the presence of micromolar calcium and is inhibited by more than 50% at 1 mM free calcium. The KD values for isradipine and devapamil are somewhat lower with the purified CaCB-receptor than with the membrane bound receptor. However, the stoichiometry of each binding site is between 0.7 and 0.9 sites per mol $\alpha_1$-subunit. These values are obtained if the binding experiments are carried out at 4° C. The binding at higher temperature depends on the calcium concentation, is often unstable and requires determination of the equilibrium time.

The CaCB-receptor and ligand concentrations given for the photoincorporation experiments result in a 1:1 stoichiometry of receptor and ligand. The described condition leads to the covalent modification of 5–9% and 3% of the dihydropyridine and phenylalkylamine binding sites, respectively. Optimal incorporation rates are only observed if the thickness of the receptor ligand solution is kept between 1 and 2 mm during photoincorporation.

The following references, and any other references cited herein, (except for those references in press at the time of filing of this application) are hereby incorporated by reference.

Ahlijanian M, Westenbroek R E, Catterall W A. Subunit structure and localization of dihydropyridine-sensitive calcium channels in mammalian brain, spinal cord, and retina. Neuron 1990;4:819–32.

Appel S H, Stockton-Appel V, Stewart S S, Kerman R H, Amyotrophic lateral sclerosis: Associated clinical disorders and immunologic evaluations. Arch Neurol 1986;43:234–8.

Appel V., Stewart S S, Smith G, Appel S H. A rating scale for amyotrophic lateral sclerosis: Description and preliminary evidence. Ann Neurol 1987;22:328–33.

Birnbaumer L, Perez-Reyes E, Bertrand P, et al. Molecular diversity and function of G-proteins and calcium channels. Biol Reproduction 1991;44:207–214.

Catterall W A, Segar M J, Takahaski, M, Molecular properties of dihydropyridine-sensitive calcium channels in skeletal muscle. J. Biol. Chem. 1988; 263:3535–3538.

Chaput M, Claes V, Portetelle D, et al. The neurotrophic factor neurokinin is 90% homologous with phosphohexose isomerase. Nature 1988;332:454–5.

Charcot J-M. Lecons sur les maladies du systeme nerveux. Paris: Delahage and Lecronier, 1877.

Dubel, S J, et al. Molecular cloning of the $\alpha$-1 subunit of an $\omega$-conotoxin-sensitive calcium channel, Proc. Natl Acad Sci USA 1992; 89:5058–5062.

Endo T, Scott D D, Stewart S S, et al. Antibodies to glycosphingolipids in patients with multiple sclerosis and SLE. J Immunol 1984;132:1793–7.

Engel A E, Nagel A, Fukuoka T, et al. Motor nerve terminal calcium channels in Lambert-Eaton myasthenic syndrome: Morphologic evidence for depletion and that the depletion is mediated by autoantibodies. Ann NY Acad Sci 1989;560:278–90.

Engelhardt J I, Appel S H, Killian J M. Experimental autoimmune motoneuron disease. Ann Neurol 1989;26:368–76.

Engelhardt J I, Appel S H, Killian J M. Motor neuron destruction in guinea pigs immunized with bovine spinal cord ventral horn homogenate: Experimental autoimmune gray matter disease. J Neuroimmunol 1990;27:21–31.

Engelhardt J I, Appel S H. IgG reactivity in the spinal cord and motor cortex in amyotrophic lateral sclerosis. Arch Neurol 1990;47:1210–6.

Hamilton S L, Hawkes M J, Brush K, Cook R. Subunit composition of the purified dihydropyridine binding protein from skeletal muscle. Biochem 1989;28:7820–8.

Hamilton S L, Tate C. Proteins involved in the uptake and release of $Ca^{2+}$ from the sarcoplasmic reticulum. In: McCormack ed. Cellular calcium: A practical approach. Oxford: Oxford Univ Press, (in press).

Hauser S L, Cazenave P A, Lyon-Caen O, et al. Immunoblot analysis of circulating antibodies against muscle proteins in amyotrophic lateral sclerosis and other neurologic diseases. Neurology 1986;36:1614–18.

Hofmann F, Flockerzi V, Nastainczyk W, Ruth P, Schneider T. The molecular structure and regulation of muscular calcium channels. Curr Top Cell Regul 1990;31:223–239.

Horwich M S, Engel W K, Chauvin P B. Amyotrophic lateral sclerosis sera applied to motor neurons. Arch Neurol 1974;30:332–3.

Hui A, Ellinor P T, Krizanova O, et al. Molecular cloning of multiple subtypes of a novel rat brain isoform of the $\alpha_1$ subunit of the voltage-dependent calcium channel. Neuron 1991;7:35–44.

Imagawa T, Smith J S, Coronado R, Campbell K P. Purified ryanodine receptor from skeletal muscle sarcoplasmic reticulum is the $Ca^{2+}$-permeable pore of the calcium release channel. J Biol Chem 1987;262:16636–43.

Ingvar-Marden M, Regli F, Steck A J. Search for antibodies to skeletal muscle proteins in amyotrophic lateral sclerosis. Arch Neurol Scand 1986;74:218–23.

Kim Yi, Neher E. IgG from patients with Lambert-Eaton syndrome blocks voltage-dependent calcium channels. Science 1988;239:405–8.

Lacerda A E, Kim H S, Ruth P, et al. Normalization of current kinetics by interaction between the $\alpha_1$ and $\beta$ subunits of the skeletal muscle dihydropyridine-sensitive $Ca^{2+}$ channel. Nature 1991;352:527–30.

Lang B, Newsom-Davis J, Peers C, et al. The effect of myasthenic syndrome antibody on presynaptic calcium channels in the mouse. J. Physiol 1987;390:257–70.

Maclennan D H, Wary P T. Isolation of a calcium sequestering protein from sarcoplasmic reticulum. Proc Natl Acad Sci USA 1971;68:1231–5.

Meininger V, Duarte F, Binet S, et al. Serum monoclonal immunoglobulins in amyotrophic lateral sclerosis: A quantitative analysis using a new Western Blot technique. Neurology 1990;40(suppl 1):183.

Mintz I M, Venena V J, Adams M E, Bean B P. Inhibition of N- and L-type $Ca^{2+}$ channels by the spider venom toxin $\omega$ Aga-IIIA. Proc Natl Acad Sci USA 1991;88:6628–31.

Morton M E, Froehner S C. The $\alpha_1$ and $\alpha_2$ polypeptides of the dihydropyridine-sensitive calcium channel differ in developmental expression and tissue distribution. Neuron 1989;2:1499–1506.

Mulder D W, Espinosa R E. Amyotrophic lateral sclerosis: Comparison of the clinical syndrome in Guam and the United States. In: Norris F H Jr., Kurland L T, eds. Motor neuron diseases. New York: Grune and Stratton, 1969:12–9.

Mulder D W, Kurland L T, Offard K P, Beard C M. Familial adult motor neuron disease: amyotrophic lateral sclerosis. Neurology 1986;36–511–17.

Nagayama Y, Wadsworth H L, Russo D, et al. Binding domains of stimulatory and inhibitory thyrotropin (TSH) receptor autoantibodies determined with chimeric TSH-Lutropin/chorionic gonadatropin receptors. J Clin Invest 1991;88:336–40.

Norman R I, Burgess A J, Harrison T M. Monoclonal antibodies against calcium channels. Ann NY Acad Sci 1989;560:258–68.

Oldstone M B A, Wilson C B, Perrin L H, et al. Evidence for immune complex formation in patients with amyotrophic lateral sclerosis. Lancet 1976;2:977–99.

Ordonez G, Sotelo J. Antibodies against fetal muscle proteins in serum from patients with amyotrophic lateral sclerosis. Neurology 1989;39:683–6.

Palo J, Rissanan A, Jolinen E, et al. Kidney and skin biopsy in amyotrophic lateral sclerosis. Lancet 1978;1:1270.

Perez-Reyes E, Kim H S, Lacera A E, Horne et al., Induction of calcium currents by the expression of the $\alpha$-subunit of the dihydropyridine receptor from skeletal muscle, Nature 1989; 340:233–236.

Pestronk A, Adams R N, Cornblath D, et al. Patterns of serum IgM antibodies to GM1 and GD1a ganglioside in ALS. Ann Neurol 1989;25:98–102.

Rowland L P. Motor neuron diseases and amyotrophic lateral sclerosis. TINS 1984;7:110–2.

Sakamoto J, Campbell K P. Isolation and biochemical characterization of the rabbit brain $\omega$-conotoxin GVIA receptor. Physiologist 1991;34:109.

Schneider T, Regulla S, Nastainczyk W, Hofmann F. Purification and structure of L-type calcium channels. In:Longstaff A. ed. Techn Mol Neurobiol. Human Press (in press).

Siddique T, Filewicz D, Pericak-Vance M A, et al. Linkage of a gene causing familial amyotrophic lateral sclerosis to chromosome 21, and evidence of genetic locus heterogeneity. New Engl J Med 1991;324:1381–4.

Sieber M et al. Eur J. Biochem 1987; 167:117–122.

Snyder et al., The 165-KDa peptide of the purified skeletal muscle dihydropyridine receptor contains the known regulatory sites of the calcium channel, Soc. Neuroscience Meeting (New Orleans) Nov. 1991.

Stefansson K, Marton L S, Dieperink M E, Circulating autoantibodies to the 200,000-dalton protein of neurofilaments in the serum of healthy individuals. Science 1985;228:1117–9.

Tajti, J., Appel, S. H., Stefani, E., Cyclophosphamide alters the clinical and pathological expression of experimental autoimmune gray matter disease. J Neuroimmunol 1991;34:143–51.

Tanabe T, Takashima H, Mikami A, et al., Primary structure of the receptor for calcium channel blockers from skeletal muscle, Nature 1987; 328:313–318.

Touzeau G, Kato A C. ALS serum has no effect on three enzymatic activities in cultured human spinal cord neurons. Neurology 1986;36:573–6.

Vincent, A, Lang B, Newsom-Davis J. Autoimmunity to the voltage-gated calcium channel underlies the Lambert-Eaton myasthenic syndrome, a paraneoplastic disorder. Trends Neurosci 1989;12:496–502.

Westenbroek R E, Ahlijanian M K, Catterall W A. Clustering of L-type $Ca^{2+}$ channels at the base of major dendrites. Nature 1990;347:281–4.

Williams D B, Windebank A J. Motor neuron disease (amyotrophic lateral sclerosis). Mayo Clin Proc 1991;66:54–82.

Younger D S, Rowland L P, Latov N, et al. Motor neuron disease and amyotrophic lateral sclerosis: Relation of high CSF protein content to paraproteinemia and clinical syndromes. Neurology 1990;40.595–9.

What is claimed is:

1. A method useful in the diagnosis of amyotrophic lateral sclerosis or the evaluation of the progression of that disease which comprises (a) contacting purified L-type skeletal muscle calcium channel complex with a biological fluid obtained from an individual suspected of having or having amyotrophic lateral sclerosis for a time and under conditions sufficient for said calcium channel complex and anti-calcium channel complex antibodies that may be present in the biological fluid to form an antigen/antibody complex; and (b) determining the presence or absence of said antigen/antibody complex to aid in the diagnosis or prognosis of amyotrophic lateral sclerosis, wherein the presence of said antigen/antibody complex is suggestive of amyotrophic lateral sclerosis in the individual or the presence of an elevated level of said antigen/antibody complex is suggestive of a more rapid progression of amyotrophic lateral sclerosis in the individual.

2. The method of claim 1 wherein said biological fluid is serum.

3. The method of claim 1 where said biological fluid is purified immunoglobulin isolated from serum.

4. The method of claim 1 wherein the method is an ELISA procedure.

5. The method of claim 1 wherein the method is an immunoblot procedure.

6. The method of claim 1 wherein the method is a direct assay.

7. The method of claim 1 wherein said step of determining comprises adding a labeled antibody to human immunoglobulin and determining the presence or absence of the label.

8. The method of claim 1 wherein the biological fluid is serum, the purified skeletal muscle L-type calcium channel complex is immobilized on a solid support, and prior to the determining step, components of the serum which did not form an antigen/antibody complex with the immobilized calcium channel complex are washed away.

9. The method of claim 8 wherein said step of determining is carried out by adding a labeled antibody to human immunoglobulin, washing away unreacted antibody to human immunoglobulin, and determining the presence of the label.

10. A method useful in the diagnosis of amyotrophic lateral sclerosis (ALS) or the evaluation of the progression of that disease which comprises (a) contacting central N-type calcium channel complex with a biological fluid obtained from an individual suspected of having or having amyotrophic lateral sclerosis for a time and under conditions sufficient for said central N- type calcium channel complex and anti-calcium channel complex antibodies that may be present in the biological fluid to form an antigen/antibody complex; and (b) determining the presence or absence of said antigen/antibody complex to aid in the diagnosis or prognosis of ALS, wherein the presence of said antigen/antibody complex is suggestive of amyotrophic lateral sclerosis in the individual or the presence of an elevated level of said antigen/antibody complex is suggestive of a more rapid progression of amyotrophic lateral sclerosis in the individual.

11. A method useful in the diagnosis of amyotrophic lateral sclerosis or the evaluation of the progression of that disease which comprises (a) contacting purified $\alpha_1$ subunit of L-type skeletal muscle calcium channel complex with a biological fluid obtained from an individual suspected of having, or suffering from, amyotrophic lateral sclerosis for a time and under conditions sufficient for the subunit and anti-subunit antibodies in said biological fluid to form an antigen/antibody complex; and (b) determining the presence or absence of said complex in order to aid in amyotrophic lateral sclerosis diagnosis or prognosis, wherein the presence of said antigen/antibody complex is suggestive of amyotrophic lateral sclerosis in the individual or the presence of an elevated level of said antigen/antibody complex is suggestive of a more rapid progression of amyotrophic lateral sclerosis in the individual.

* * * * *